US006511430B1

(12) United States Patent
Sherar et al.

(10) Patent No.: US 6,511,430 B1
(45) Date of Patent: Jan. 28, 2003

(54) USE OF HIGH FREQUENCY ULTRASOUND IMAGING TO DETECT AND MONITOR THE PROCESS OF APOPTOSIS IN LIVING TISSUES, EX-VIVO TISSUES AND CELL-CULTURE

(75) Inventors: Michael D. Sherar, Toronto (CA); Gregory J. Czarnota, Mississauga (CA); John Hunt, Toronto (CA); Michael Kolios, Toronto (CA)

(73) Assignee: University Health Network, Toronto (CA)

( * ) Notice: Subject to any disclaimer, the term of this patent is extended or adjusted under 35 U.S.C. 154(b) by 0 days.

(21) Appl. No.: 09/763,183
(22) PCT Filed: Aug. 19, 1999
(86) PCT No.: PCT/CA99/00770
§ 371 (c)(1),
(2), (4) Date: May 8, 2001
(87) PCT Pub. No.: WO00/11468
PCT Pub. Date: Mar. 2, 2000

Related U.S. Application Data

(60) Provisional application No. 60/097,115, filed on Aug. 19, 1998.

(30) Foreign Application Priority Data

Aug. 19, 1998 (US) .......................................... 60/097115

(51) Int. Cl.⁷ ................................................. A61B 8/00
(52) U.S. Cl. .......................... 600/443; 600/437; 601/2; 601/3
(58) Field of Search ........................ 601/2, 3; 600/443, 600/437

(56) References Cited

PUBLICATIONS

Miller et al., Backscatter Imaing and Myocardial Tissue Characterization, Department of Physics and Cardiovascular Division, Washington University, St. Lousi, Missouri, pp. 1–31.*
Sherar et al., *Ultrasound backscatter microscopy images the internal structure of living tumour spheroids*, Nature, vol. 330, No. 6147, pp. 493–495.

Bérubé et al., *Use of a high frequency ultrasound microscope to image the action of 2–nitroimidazoles in mutlicellular spheroids, Br. J. Cancer* (1992), 65, pp. 633–640.
Hockenberry, David, *Defining Apoptosis Am. J. Pathol* (1995), vol. 146, No. 1, pp. 16–19.
Majno, Guido et al., *Apoptosis, Oncosis, and Necrosis An Overview of Cell Death Am. J. Pathol.* (1995), vol. 146, No. 1, pp. 3–15.
Fraser A., et al., *A License to Kill Cell* (1996), vol. 85, pp. 781–784.
Lizzi, Frederic, et al., *Theoretical framework for spectrum analysis in ultrasonic tissue characterization J. Accoust. Soc. Am.* (1983), vol. 73, No. 4, pp. 1366–1373.
Hall, Timothy J., et al., *Describing small–scale structure in random media using pulse–echo ultrasound J. Acoust. Soc. Am.*, (1990), vol. 87, No. 1, pp. 179–192.
Hall, Timothy J., et al., *Parametric Ultrasound Imaging from Backscatter Coefficient Measurements: Image Formation and Interpretation Ultrasonic Imaging*, (1990), vol. 12, pp. 245–267.

* cited by examiner

Primary Examiner—Marvin M. Lateef
Assistant Examiner—Ruby Jain
(74) Attorney, Agent, or Firm—Crowell & Moring LLP

(57) ABSTRACT

A non-invasive method of monitoring apoptosis in cell culture, ex-vivo tissues and in-vivo tissues using high frequency ultrasound imaging is provided. The method includes the steps of: 1) imaging a selected site of the cell culture or tissues using high frequency (above 20 MHz) ultrasound imaging (before image); 2) exposing the selected site to an apoptosis-inducing stress; 3) imaging the selected site or a portion thereof, using ultrasound imaging at subsequent timed intervals (after image(s)); 4) measuring the signal amplitude of a region of interest of the selected site in the before and after images; 5) comparing the signal amplitude measurements for the regions of interest in the before and after images and determining whether the after image regions exhibit an increase in amplitude as compared to the before image regions which is an indication that apoptosis has begun; and 6) measuring the change in the frequency spectrum of the radiofrequency ultrasound backscatter signal in the region of interest in the before and after images and confirming that apoptosis has begun when the slope of the frequency spectrum has increased.

7 Claims, 16 Drawing Sheets

Figure 1A:
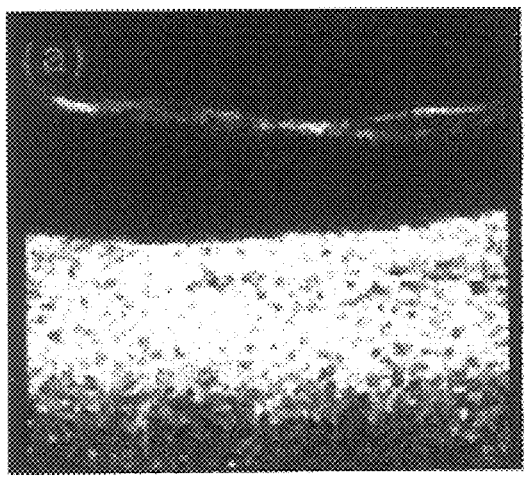
Figure 1B:
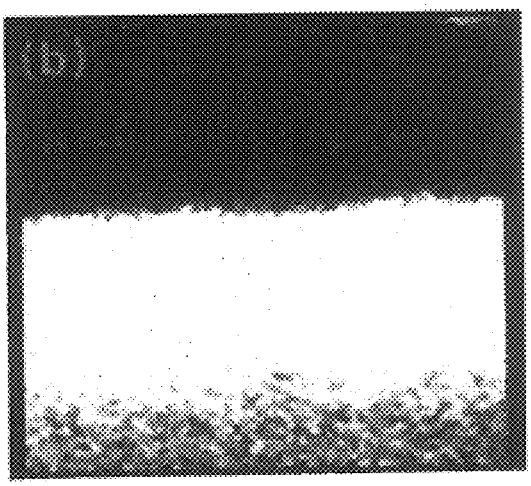
Figure 1C:
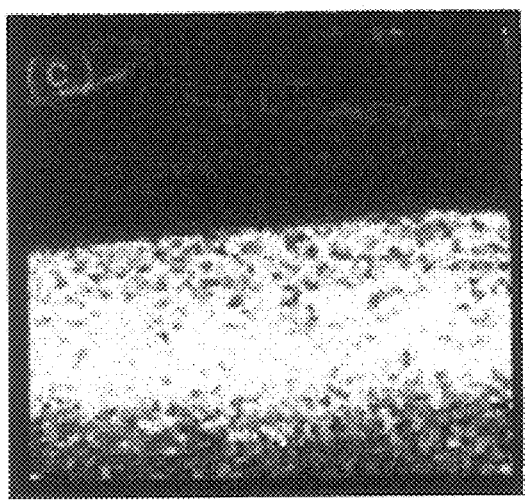

USE OF HIGH FREQUENCY ULTRASOUND IMAGING TO DETECT AND MONITOR THE PROCESS OF APOPTOSIS IN LIVING TISSUES, EX-VIVO TISSUES AND CELL-CULTURE

This application claims benefit of provisional application 60/097,115 filed Aug. 19, 1998.

FIELD OF THE INVENTION

The present invention relates to a non-invasive method for detecting and monitoring apoptosis. In particular, the present invention relates to a method for detecting apoptosis using ultrasound imaging.

BACKGROUND OF THE INVENTION

Ultrasound imaging is one of the commonest radiological modalities presently used in clinical medicine. It is used to image the developing fetus, to image organs and vascular components, and to image tumours. Recently, high frequency ultrasound based systems have been developed to produce high resolution images of biological specimens such as spheroids or human tissues in vivo.

High frequency ultrasound imaging has been used to investigate the living and hypoxic regions of cell spheroids indicating the ability of this imaging modality to differentiate different types of cellular morphologies (Sherar et al., Ultrasound backscatter microscopy images the internal structure of living tumour spheroids, *Nature* 1987; 330: 493–495; Bérubé et al., Use of a high frequency ultrasound microscope to image the action of 2-nitroimidazoles in multicellular spheroids, *Br J Cancer,*1992; 65: 633–640).

Apoptosis is one mechanism by which biological cells undergo cell death. It plays a significant role in both normal and disease-related biological processes (Hockenbery, D. Defining apoptosis. *Am J Pathol,* 1995; 146: 16–19; Majno G., Joris I. Apoptosis, oncosis, and necrosis. *Am. J Pathol,* 1995; 146: 3–15; Fraser A., Evan G. A view to a kill. *Cell,*1996;85: 781–784). In addition, cells undergo apoptosis in response to a variety of stresses including chemotherapy, radiation therapy, photodynamic therapy and heat. It is useful in both experimental and clinical applications to know whether cells are undergoing apoptosis. This is currently determined by taking samples of the cells or tissues of interest and observing, using histological and DNA measurement methods, whether the cells exhibit the morphological changes that are indicative of apoptosis. These changes include membrane blebbing, DNA condensation and DNA fragmentation. However, these methods are not only invasive, but also time-consuming, requiring processing of a cell or tissue sample before data relating to apoptosis can be obtained.

The ability to differentiate apoptotic cells from living or otherwise dead cells non-invasively in-vitro and in vivo would potentiate clinical diagnoses, the understanding of disease processes and normal biological processes that involve apoptosis, and provide a more efficient way of studying apoptosis in response to therapeutic agents.

SUMMARY OF THE INVENTION

Accordingly, the present invention provides a non-invasive method of monitoring apoptosis in cell culture, ex-vivo tissues and in-vivo tissues using high frequency ultrasound imaging, which comprises the steps of 1.) imaging a selected site of the cell culture or tissues using high frequency (above 20 MHz) ultrasound imaging (before image);

2.) exposing the selected site to an apoptosis-inducing stress;

3.) imaging the selected site or a portion thereof, using ultrasound imaging at subsequent timed intervals (after image(s));

4.) measuring the signal amplitude of a region of interest of the selected site in the before and after images;

5.) comparing the signal amplitude measurements for the regions of interest in the before and after images and determining whether the after image regions. exhibit an increase in amplitude as compared to the before image regions which is an indication that apoptosis has begun; and 6.) measuring the change in the frequency spectrum of the radiofrequency ultrasound backscatter signal in the region of interest in the before and after images and confirming that apoptosis has begun when the slope of the frequency spectrum has increased.

In another aspect of the invention, further confirmation of the occurrence of apoptosis is achieved by the step of calculating the average scatterer size in the region of interest by applying an ultrasound scattering model to the radiofrequency ultrasound signals from the regions of interest. Apoptosis is confirmed when the average scatterer size has reduced significantly according to this analysis. The decrease in scatterer size reflects the fragmentation of nuclear material that occurs during apoptosis.

More simply, the method of the invention is to use ultrasound imaging to monitor and measure the apoptotic process in cell culture, ex-vivo tissues and in-vivo tissues using the three-step process of:

1) Imaging of the treated sample or region of tissue before and during treatment and/or imaging treated and untreated regions in the sample or tissue;

2) Measurement of the change in signal amplitude or intensity in the treated and untreated samples or regions of tissue; and 3) Measurement of the change in frequency spectrum of ultrasound scatter from the treated and untreated regions.

An optional fourth step to this process is:

4) Calculation of average scatterer size from the frequency spectra collected.

In essence, the present invention offers a new use of ultrasound imaging to monitor the process of apoptosis. We have discovered that the processes of nuclear condensation and fragmentation that are indicative of apoptosis result in an approximately 3–6-fold increase in the amplitude of ultrasound scattered from cells in culture, ex-vivo tissues and in-vivo tissues as compared to normal cells not undergoing apoptosis. Also, we have discovered that the frequency spectrum of the ultrasound scattered from biological samples and tissues containing cells undergoing apoptosis is different from untreated samples not undergoing apoptosis. The specific subcellular features which permit the apoptotic phenomenon to be visualized have been investigated and are shown to be related to the changes in the cellular nuclear material cells undergo during apoptosis.

Apoptosis is indicated in the sample or region of tissue if both the signal intensity increases and the slope of the frequency spectrum increases. Further confirmation is indicated by a decrease in the average scatterer size in the treated regions. The regions of tissue that satisfy these criteria could be colour coded on the original ultrasound image, for example. There are various methods known in the art for calculating the signal amplitude, slopes of the frequency spectra and the average scatterer size parameters, and any of these may be used, with the choice being one that a person skilled in the art can select readily.

DETAILED DESCRIPTION OF THE INVENTION

The present method is a non-invasive method utilizing high frequency ultrasound imaging to detect and monitor apoptosis in cells or tissues, in vitro, in vivo or ex vivo. As will be appreciated by those of skill in the art, the term "high frequency ultrasound imaging" is meant to refer to ultrasound imaging at frequencies of greater than 20 MHz. The method involves taking high frequency ultrasound images of the cells or tissues of interest prior to the application of an apoptosis-inducing stress, herein referred to as a "before image", as well as taking a high frequency ultrasound image following application of the stress, referred to herein as an "after image". Alternatively, high frequency ultrasound images of treated and untreated regions of the sample or tissue can simultaneously be taken. In this case, the ultrasound image of the untreated region would be equivalent to the "before image" and the ultrasound image of the treated region would be equivalent to the "after image". The terms "before image" and "after image" as used herein encompass both of the foregoing alternatives.

"Apoptosis-inducing stress", as referred to herein, is meant to encompass any stress which will result in the initiation of apoptosis. Examples of apoptosis-inducing stresses include chemotherapeutic agents, drugs, photodynamic therapy, chemical modifiers aimed at protecting tissues from radiations such as sunscreens, radiations including X-rays, gamma rays and ultraviolet radiations, oxygen and/or nutrient deprivation that can occur after organ removal for transplantation for example, and the activation of genes that can initiate an apoptotic response as well as aging and developmental processes. Accordingly, the term "apoptosis-inducing stress" is also meant to encompass biological events that occur normally in tissues to induce apoptosis.

The quantitative part of the method involves either obtaining the radiofrequency signal and measuring the amplitude, which is the square root of intensity, averaged over a region of interest or if radiofrequency data is not available from the ultrasound machine, using a calibration curve from the ultrasound machine manufacturer to convert the final machine signal into an average radiofrequency amplitude over the region of interest. In either case, the signal amplitude can be measured over the region exposed to the stress and over control untreated regions at any timepoint after the stress is applied. A region of apoptosis, as a result of the treatment of the tissues/cells, is indicated where the signal amplitude rises by a significant factor, for example, where the signal amplitude rises by at least a factor of three, and more preferably by a factor of between three and six. The threshold of the increase in signal intensity that is used to indicate apoptosis in a particular biological system can be determined by correlating the change in signal intensity with a standard assay for apoptosis such as fluorescent staining of DNA when the biological system is exposed to a known apoptosis-inducing stress. A graph of the change in ultrasound signal intensity versus the percentage of apoptotic cells as measured using the standard apoptosis assay would then be the calibration curve used to determine the percentage of apoptotic cells in that biological system to any apoptosis-inducing stress using high frequency ultrasound imaging.

Subsequent to analyzing the signal amplitude data, a frequency analysis is performed on the radiofrequency ultrasound signals. This involves taking a Fourier transform of the data from both treated and untreated regions. At least 20 A-scan lines of radiofrequency data and preferably 20–50 lines are acquired from each region of interest and digitized by the ultrasound scanner. The window length over which the A-scan radiofrequency signal is digitized should correspond to between about 0.5 and 3 mm in the image. Ideally, the window length should be at the lower end of this range to reduce the effects of ultrasound attenuation in the frequency analysis. Fourier transforms of the acquired radiofrequency A-scan lines are calculated and then squared to give the Fourier power spectrum for each A-scan. The Fourier power spectrum is then normalized against a reference Fourier power spectrum of the ultrasound pulse from the transducer. This is achieved by dividing the Fourier power spectrum of the signals from the region of interest by the Fourier power spectrum of the ultrasound reflected from a hard surface such as a quartz flat. The normalized power spectra are calculated between bandwidth limits where the value of the reference Fourier power spectrum is −15 dB or 3% of the maximum value at the center frequency of the ultrasound imaging system. Linear regression is performed on the normalized power spectrum from each A-scan line. The linear regression lines fitted to each normalized Fourier power spectrum are then averaged over all the scan lines acquired from a region of interest to give an average fitted normalized Fourier power. The average fitted normalized Fourier power spectra are plotted as graphs of 10 $\log_{10}$ (normalized power) versus frequency. The slope of this line with function y=mx+c, is m. Apoptosis is indicated by the slope of the average fitted normalized Fourier power spectrum versus frequency becoming significantly more positive during treatment. An increase in the slope of at least 30% is indicative of apoptosis for cells in vitro. The increase in slope expected in tissues both ex-vivo and in-vivo varies with the particular tissue being examined. An increase in slope of at least 5% indicates apoptosis is occurring in tissues.

The method of frequency analysis described herein is well described in the literature and can be implemented readily by a person skilled in the art. The threshold of the increase in slope of the average fitted normalized Fourier power spectrum that is used in any particular biological system to indicate apoptosis can be determined by first correlating the increase in slope with a standard assay of apoptosis when a known apoptosis inducing agent is applied to that biological system. A graph of the change in slope of the average fitted normalized Fourier power spectrum versus percentage of apoptotic cells as measured using the standard apoptosis assay would then be the calibration curve used to determine the percentage of apoptotic cells in that biological system due to any apoptosis-inducing stress using high frequency ultrasound imaging.

Other methods in addition to our preferred method of Fourier analysis may be used to measure the change in the radiofrequency ultrasound signals due to apoptosis reflected back from the tissue or cells for example the increase in ultrasound signal due to apoptosis can be measured by calculating the mid-band fit of the average normalized Fourier power spectrum. The "mid-band fit" as referred to herein is defined as the value of the average normalized Fourier power spectrum at the center frequency of the chosen bandwidth. Similarly, the change in the frequency content of the ultrasound signals due to apoptosis can be measured by performing wavelet analysis, for example.

Figure 7:
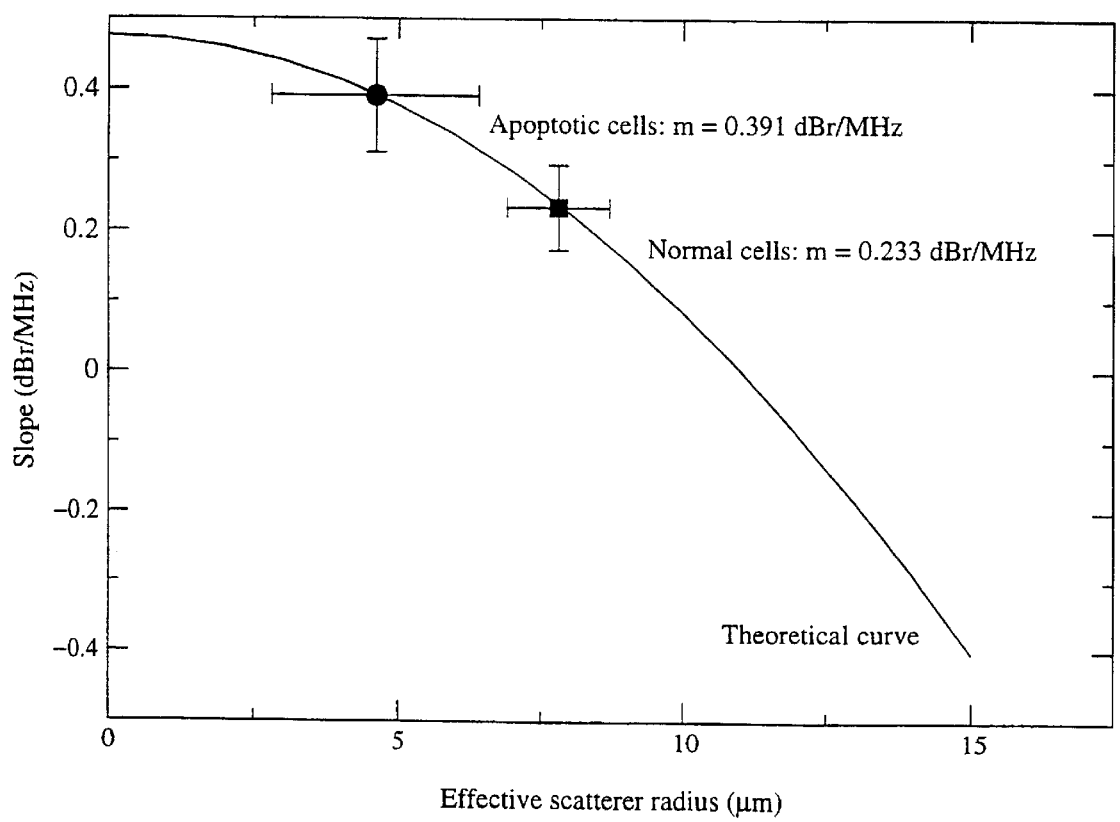

To further confirm the occurrence of apoptosis, the average scatterer size can be calculated from the radiofrequency spectra. This determination is not independent of slope calculated as set out above, and thus functions to verify apoptosis. Several methods have been published for calculating scatterer size from ultrasound backscatter signals including those of Lizzi et al (Theoretical framework for spectrum analysis in ultrasonic tissue characterization, *Journal of the Acoustical Society of America* 1983, 73, 1366–1373) and by Hall et al (Describing small-scale structure in random media using pulse echo ultrasound *Journal of the Acoustical Society of America* 1990, 87, 179–192; Parametric ultrasound imaging from backscatter coefficient measurements: Image formation and interpretation *Ultrasonic Imaging* 1990, 12, 245–267). Apoptosis is confirmed by a significant decrease in the average scatterer size in the region of interest. A decrease in scatterer size of between about 20–50% is generally indicative of apoptosis; however, decrease in scatterer size as calculated by these techniques is tissue dependent as well as dependent on the characteristics of the transducer used to calculate the theoretical curve of slope vs. scatterer radius (as shown in FIG. 7). Thus, a decrease in the scatterer size of at least 30% is more preferably indicative of apoptosis for cells in-vitro whereas a decrease in scatterer size of 20% is more preferably indicative of apoptosis for tissues both ex-vivo and in-vivo.

The threshold in decrease in scatterer size that is used to indicate apoptosis in any particular biological system can be determined by correlating the decrease in scatterer size calculated from the radiofrequency ultrasound data with the percentage of cells undergoing apoptosis as measured using a standard apoptosis assay when a known apoptosis-inducing agent is applied to that biological system. A graph of the decrease in scatterer size calculated from the ultrasound imaging radiofrequency data decrease versus percentage of apoptotic cells as measured using a standard assay would then be the calibration curve used to determine the percentage of apoptotic cells in that biological system due to any apoptosis-inducing stress using high frequency ultrasound imaging.

The present method may be more particularly characterized as follows:

1. Take ultrasound images (B-Scan or C-Scan) of the cells or tissues of interest before the apoptosis inducing treatment is applied.
2. Take a second set of images of the same area during and/or after treatment.
3. Calculate the signal level change in the region of interest. This can be achieved in two different ways: i) using a calibration curve from the ultrasound machine manufacturer to convert the final machine signal (pixel level) into an average radiofrequency signal power over the region of interest or ii) if the radiofrequency signal can be obtained from the machine, use this directly to calculate an average signal power over the region of interest.
4. The signal amplitude should be measured over a region of interest within the region of tissue exposed to the treatment, at any timepoint of interest after the treatment is applied and compared to the same region of interest in the images before the treatment was applied or compared to a neighboring area of untreated tissue.
5. An increase in signal power (intensity) by more than a factor of 9 (equivalent to an increase in signal amplitude by a factor of 3) over control or pretreatment measurements indicates that apoptosis is occurring in the treated region. In addition, the percentage of apoptotic cells in any biological system can be determined by using a calibration curve as set out above.
6. The second part of the process is to perform a frequency analysis on the radiofrequency data. The objective is to calculate the change in the slope of the average normalized Fourier power spectrum as set out above. Apoptosis is indicated if the change in slope is at least 30% for cells in vitro and at least 5% for tissues. In addition, the percentage of apoptotic cells in particular biological systems can be determined by using a calibration curve for each biological system as set out above.
7. A third calculation can be performed to confirm that the cause of changes in signal amplitude and frequency spectra slope is indeed apoptosis. This calculation derives the average scatterer size from the frequency spectra data. One method of calculating the average scatterer size is to employ the method of Lizzi et al. (supra). Apoptosis is confirmed if the average scatterer size decreases by about 20–50%, in addition to increases in the signal amplitude and the slope of the frequency spectra in the region of interest as set out above. In addition, the percentage of apoptotic cells in particular biological systems can be determined using a calibration curve for each biological system as set out above.
8. Data from the calculations above can be presented in several ways. Results of each of the individual calculations can be displayed and stored as a numeric value on the ultrasound imaging machine together with an indication as to whether they are consistent with apoptosis when compared to the threshold values set out above. Similarly, the percentage of apoptotic cells can be displayed and stored. In the preferred embodiment, increases in both signal intensity and slope of the average normalized Fourier power spectrum over the thresholds set out above would be required to report a positive finding that apoptosis is occurring in the sample as a result of the apoptosis-inducing stress.

It has been determined that the origin of the contrast in both signal amplitude and frequency spectrum in cells undergoing apoptosis is due to DNA condensation and fragmentation. This results in several ultrasound scattering DNA fragments being present in the apoptotic cell. Simulation studies show that this production of scattering particles in the cell during apoptosis should lead to a 3–6-fold increase in scatter amplitude signal and a 5% to 30% increase in the slope of the frequency spectrum, depending on the sample (i.e. cells vs. tissues).

The present invention has many potential applications. These include but are not restricted to human and veterinary, diagnostic and therapeutic applications. Such applications include the testing of drugs and other chemical compounds for toxicity mediated by apoptosis, the study of the effects of oncogenes and other genes on apoptosis and the measurement of the viability of organs and tissues for transplantation. The invention can be used and studied for these applications in cells in-vitro, in human and animal tissues ex-vivo and in-vivo and for specific clinical applications including the monitoring of patient responses to therapies including chemotherapy, radiation therapy, photodynamic therapy, gene therapy and any other therapy that may involve the triggering of an apoptotic response in cells. An example is to monitor apoptosis in inflammatory tissues after triggering of the immune system, which is a potential treatment for immune disorders. Further applications include studying the effects of ultraviolet, X-ray and gamma radiation on cells and tissues as well as chemical modifiers such as sunscreens aimed at protecting tissues from these radiations.

The present invention can be applied to several different ultrasound imaging methods. These methods include the use of external transducers that can be used to image tissues such as the skin and eye, invasive interstitial needle-based transducers that can be inserted directly into a target tissue deep within the body such as a tumour or normal tissue, intraluminal catheter-based transducers that are designed to image from within arteries for example and endoscopic or intracavitary ultrasound systems that can be used to image tissues including the easophagus and colon for example.

DESCRIPTION & DISCUSSION OF THE DRAWINGS

The accompanying drawings, reference to which is made in the specific examples which follow, are used to illustrate the invention and may be used to interpret the scope of the claims, but not to limit them unnecessarily.

FIG. 1 illustrates ultrasonic images of (a) viable, (b) apoptotic, (c) viable cells that were heat-killed, and (d) heat-treated apoptotic cells. The cells used here and in all subsequent in-vitro experiments were human acute myeloid leukemia (AML-5) cells. Images are original ultrasonograms. The bright horizontal band in each panel corresponds to the focal region in the ultrasonic image. The images are oriented such that the top of each sample is approximately half way from the bottom of each panel. Any speckle pattern above this corresponds to debris in the buffered solution in which the pellets were immersed for imaging purposes. Scale bar represents 1 mm.

FIG. 2 illustrates light microscopic images of (a) viable, (b) apoptotic, (c) heat-killed cells, and (d) heat-treated apoptotic cells. All uncertainties in this caption are expressed as standard deviations. (a) Viable cells exhibited a mean diameter of 6.12±0.6 $\mu$m and a nucleus with a mean diameter of 4.6±0.6 $\mu$m. (b) The apoptotic cells exhibited a mean diameter of 7.1±0.8 $\mu$m, and on average 5.1±1.8 highly condensed nuclear regions with a mean length of 1.3±0.6 $\mu$m and a mean width of 0.81±0.4 $\mu$m. (c). The heat-killed cells exhibited a slight enlargement in size to a diameter of 7.2±1 $\mu$m with a nucleus with a mean diameter of 4.7±0.6 $\mu$m and a predominance of granular features with sizes of 0.5–1.3 $\mu$m. (d) The heated apoptotic cells did not show a size difference in comparison to the apoptotic sample and also exhibited increased non-nuclear granular features. Cells were prepared for microscopy as standard histological cell smears and were stained with haematoxylin and eosin. All size measurements were carried out with a sample size of 50. Scale bar represents 20 $\mu$m.

Figure 3A:
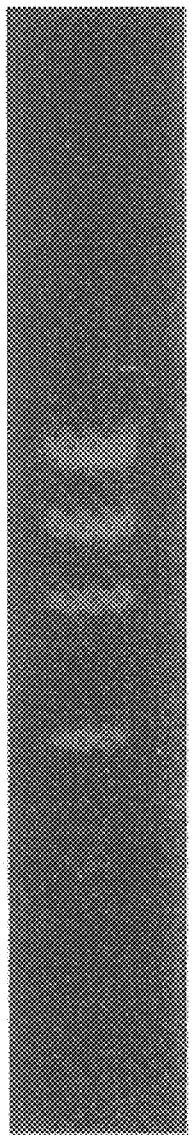
Figure 3B:
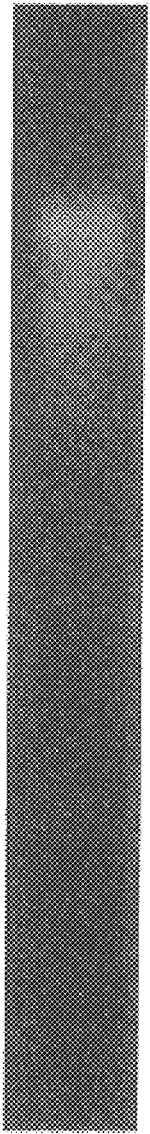
Figure 3C:
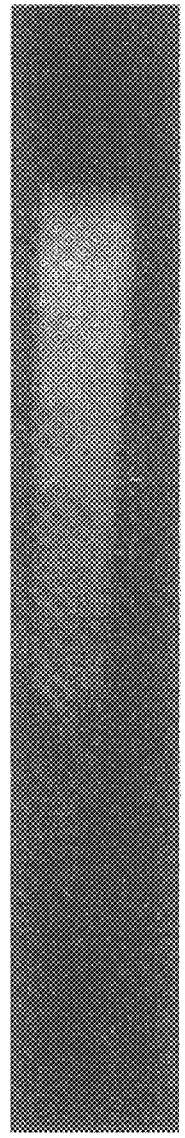

FIG. 3 illustrates DNA-electrophoretic analysis of viable and apoptotic cells. (a) $\phi$X174× Hae III DNA markers. From top to bottom: 1353, 1078, 872, 603 base-pairs double stranded DNA. (b) Purified DNA from viable cells. (c) Purified DNA from apoptotic cells exhibiting DNA laddering fragmentation pattern.

Figures 4A, 4B, 4C, 4D, 4E:

FIG. 4 illustrates the results of ultrasound imaging of apoptotic cells. Each panel is a representative ultrasound scan of a pellet of AML-5 cells. The width of each panel is 4 mm. The bottom of each ultrasound scan is at the bottom of each frame. Pellets are immersed in buffered saline. From left to right panels correspond to cells treated with cisplatinum for 0, 6, 12, 24 and 48 hours to induce varying degrees of apoptosis. A bar at the bottom right of the figure indicates the colour map used in this image, the left of the bar indicating the colour that corresponds to pixel values of 0 and the right giving the colour that corresponds to a pixel value of 256. At 0, 6, 12, 24, and 48 hours, histological analysis indicated that 1.6, 2, 36, 87 and 93% of all cells showed nuclear fragmentation, respectively. At the 6 hour timepoint 72% of the cells exhibited prominent nuclear condensation changing from a nuclear diameter 70% of the cellular diameter before addition of the drug, to a diameter 40% of the cellular diameter at 6 hours. After the 6-hour timepoint 95% of all cells exhibited nuclear condensation of fragmentation.

Figure 5A:
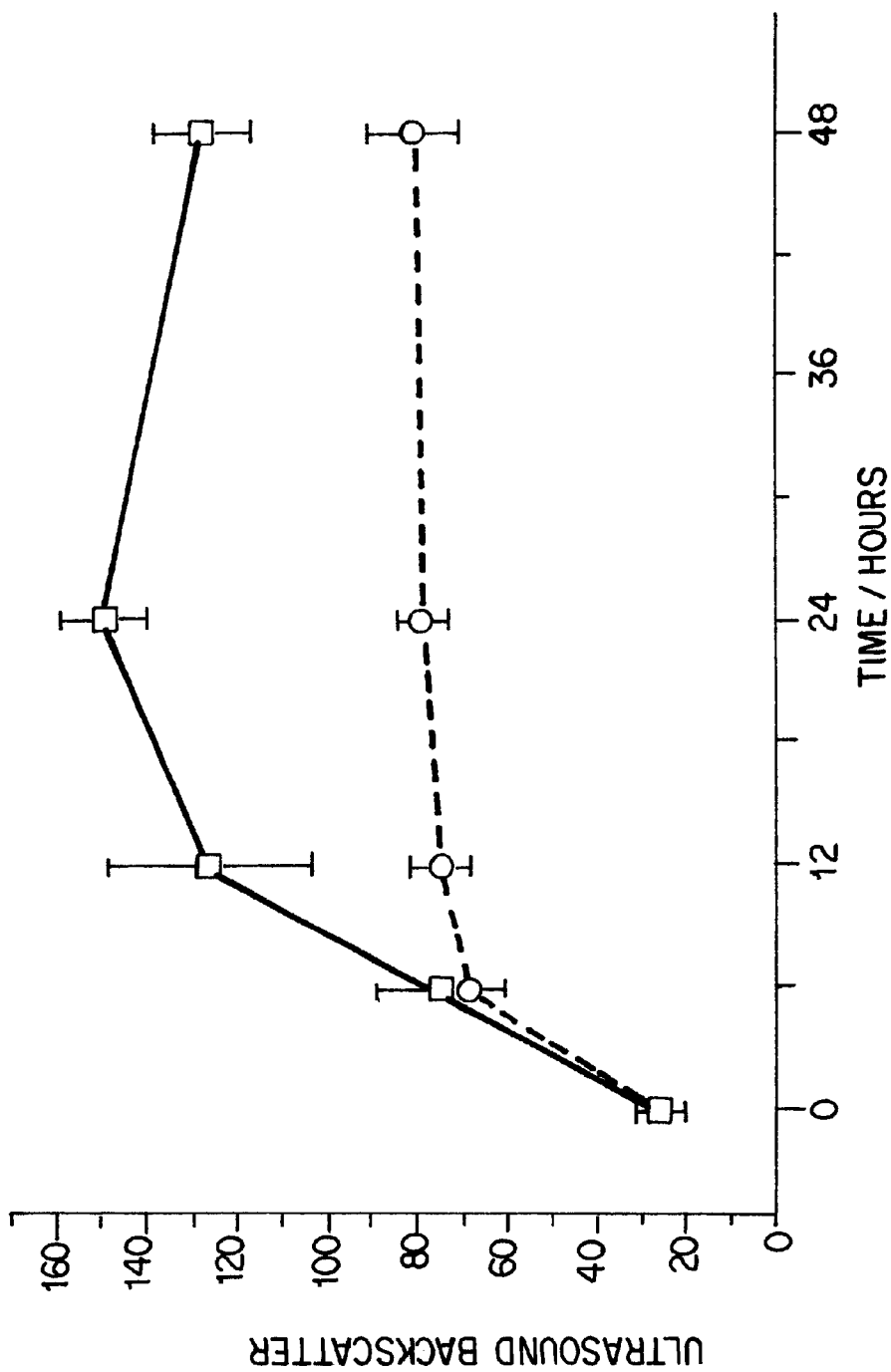
Figure 5B:
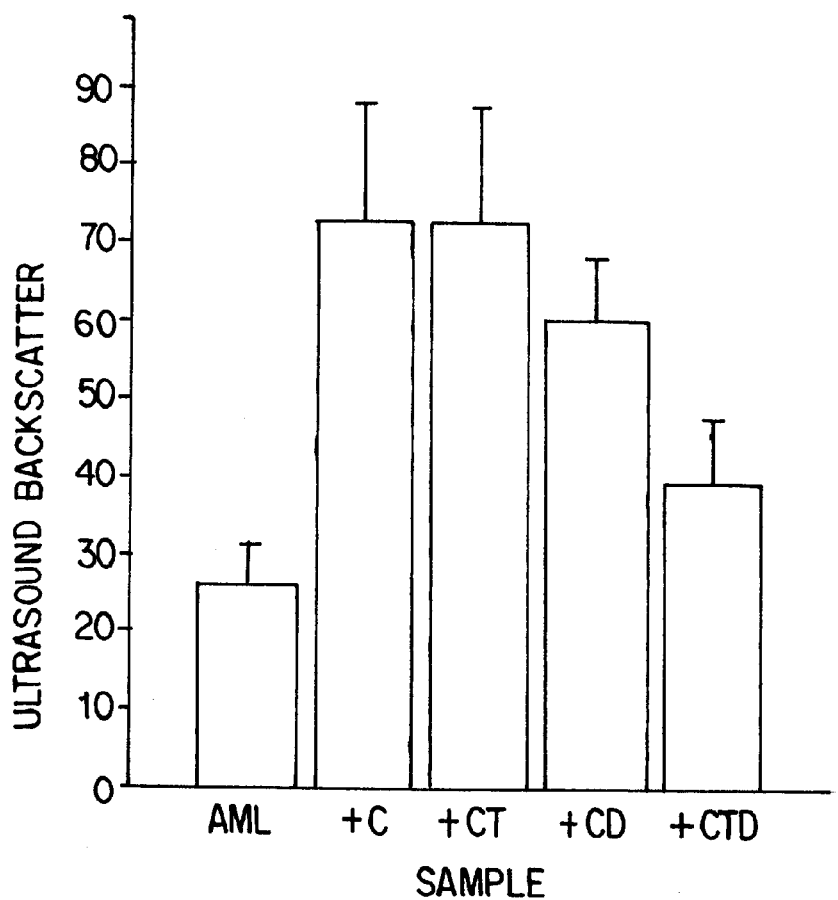
Figures 5C, 5D, 5E, 5F:
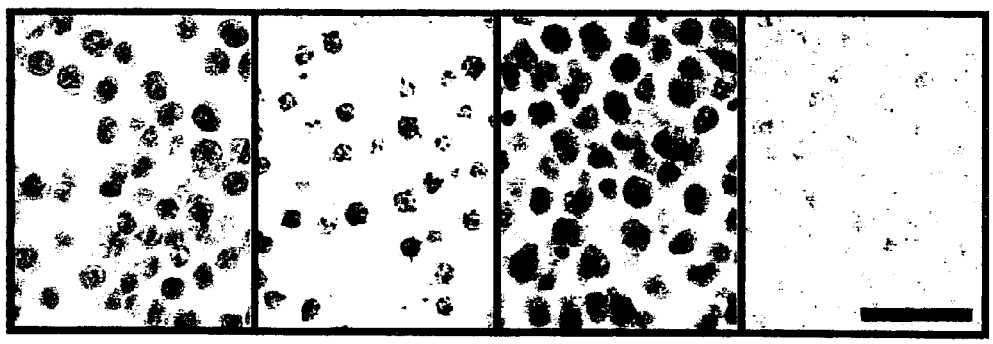

FIG. 5(A) illustrates results of relative ultrasound backscatter measurements for apoptotic and mitotically-enriched AML cells. Relative ultrasound backscatter amplitude is plotted against drug exposure time for cisplatinum treated apoptotic cells (solid line) and colchicine treated mitotically enriched cells (dashed line). In the cisplatinum treated cells onset of nuclear fragmentation after nuclei have condensed (6 hours) further increases the scatter from 2.92-fold to 5.83-fold that of untreated cells. FIG. 5(B) illustrates results indicating nuclear condensation is directly associated with increased ultrasound backscatter. Ultrasound backscatter amplitude measurements show that colchicine treated cells (+C) scatter ultrasound 2.83±1.2 times greater than the non-treated cells (AML). Addition of Triton X-100™ alone to the colchicine exposed cells (+CT) did not change the backscatter. Adding DNase alone to the cells only slightly lowered the backscatter (+CD). Adding DNase and permeabilizing Triton X-100™ (+CTD) lowered the ultrasound backscatter towards that of the untreated cells. Results shown are for the higher of two DNase concentrations used. The lower level generated results intermediate between the colchicine exposed cells and samples treated with the higher DNase concentration. FIG. 5(C) illustrates representative histological analyses of AML cells. From left to right panels correspond to untreated viable cells, cells treated with cisplatinum for 24 hours (apoptotic), cells treated with colchicine for 24 hours (mitotically enriched), and mitotically enriched cells treated with an excess of DNase I to digest condensed DNA. Control samples treated with DNase alone or permeabilizing agent alone are histologically equivalent to the mitotically enriched population. The untreated cells exhibited a diameter of 6.0±0.8 $\mu$m and have nuclei which are circular in cross-section with a diameter of 4.5±0.8 $\mu$m. The cisplatinum treated apoptotic cells, shown at 24 hours after addition of drug, had a slightly larger diameter of 6.4±0.8 $\mu$m and prominent fragmented nuclei. On average, each cells had 3.9±2.1 nuclear fragments that were 2.0±1.8 $\mu$m in length and 1.3±0.8 $\mu$m in width. The colchicine treated mitotically enriched cells exhibited prominent mitotic figures. These cells were 6.2±1.0 $\mu$m in diameter and had nuclear regions 4.3±1.0 $\mu$m in mean diameter. After treating such mitotically enriched cells with permeabilizing agent and DNase their histological appearance changed (rightmost panel). The prominent nuclear staining of the colchicine treated cells was no longer present and the cells appeared more like untreated cells with respect to their staining characteristics. These cells were unchanged in size after exposure to DNase; they had a mean diameter of 6.2±1.1 $\mu$m and had pink staining nuclear regions that were 4.4+1.3 $\mu$m in mean diameter. All values given are ±1 standard deviation. The scale bar indicates 20 $\mu$m.

Figure 6:
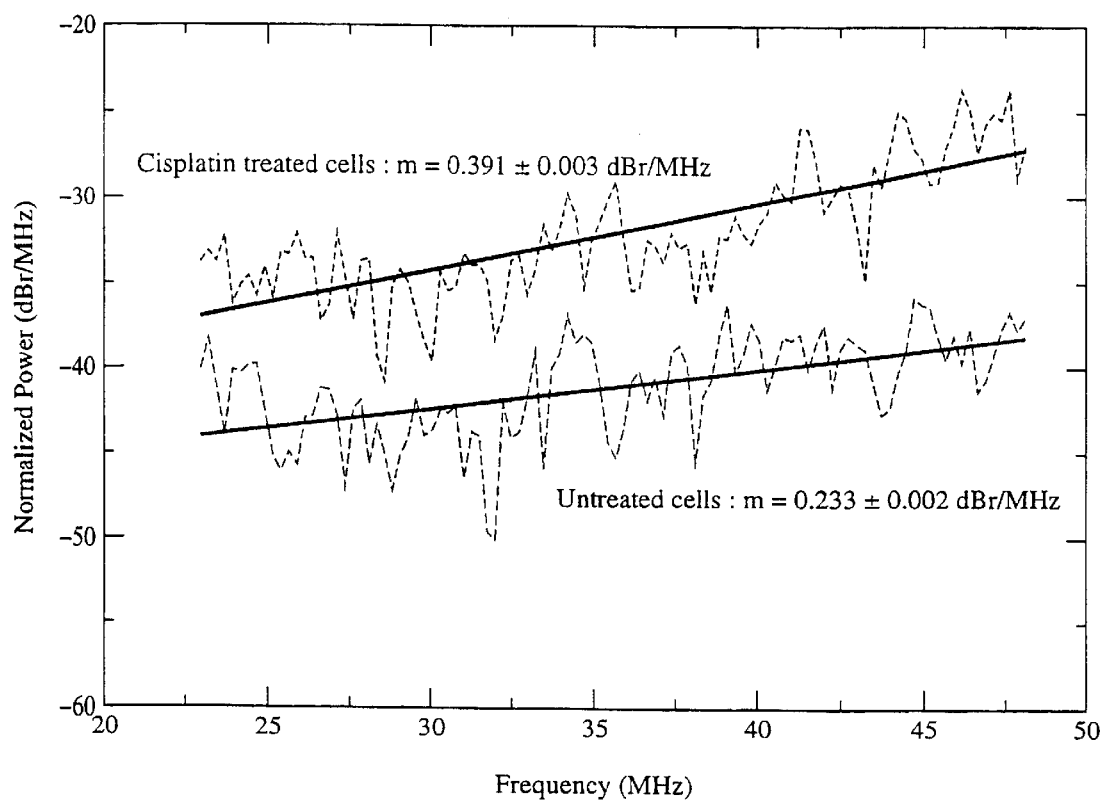

FIG. 6 illustrates the results of frequency spectra analysis for normal and apoptotic cells. Here Acute Myeloid Leukemia Cells (AML-5 cells) were grown in suspension and treated with cisplatinum. 24 hours after addition of the drug, cells were spun down into pellets and high frequency ultrasound B-scans were taken. Radiofrequency spectra were collected for treated and untreated pellets of cells. The dotted lines represent the average normalized Fourier power spectrum averaged over 30 independent radiofrequency A-scan lines each with a 3 mm window length in the axial direction. The solid lines are the average fitted normalized Fourier power spectra for the apoptotic and normal cells as indicated. An increase in the slope of the average fitted normalized Fourier power spectra due to apoptosis is observed.

FIG. 7 shows the results of calculating the scatterer average scatterer size for both normal and apoptotic cells. Using the method of Lizzi et al (Supra), a theoretical calibration curve of the slope of the average normalized Fourier power spectrum versus effective scatterer size was produced (solid line). This theoretical calibration curve was calculated from the specific transducer parameters (bandwidth) and region of interest parameters (window size) used in this experiment. The effective scatterer sizes were then determined from the experimentally determined slope of the of the average normalized Fourier power spectrum. The effective scatterer size as calculated is 7.5 micrometers for the normal cells and 4 micrometers for the apoptotic cells.

Figure 8A:
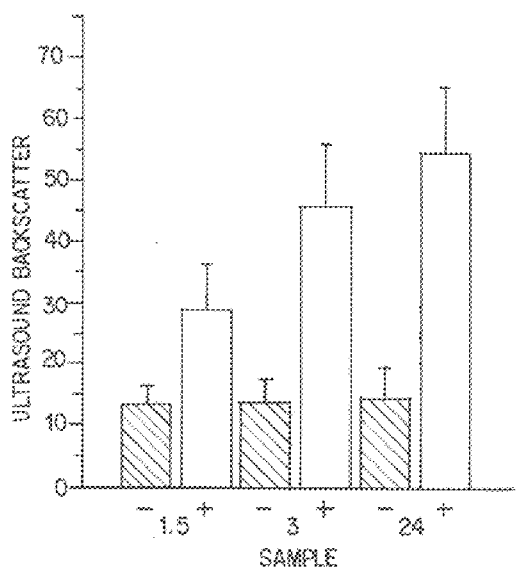
Figures 8B, 8C:
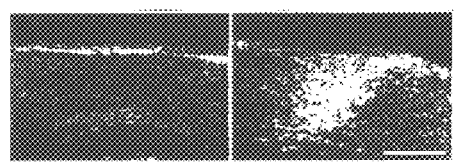
Figure 9A:
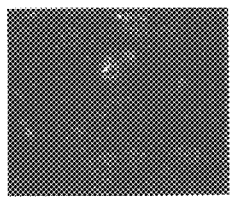
Figure 9B:
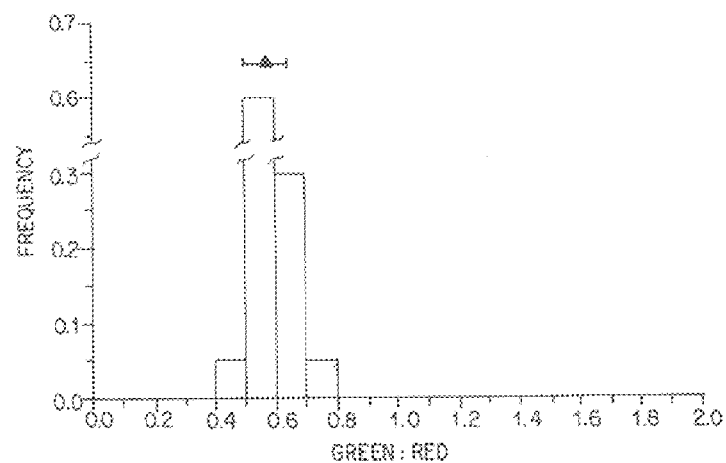
Figure 9C:
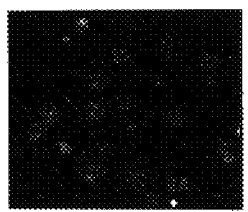
Figure 9D:
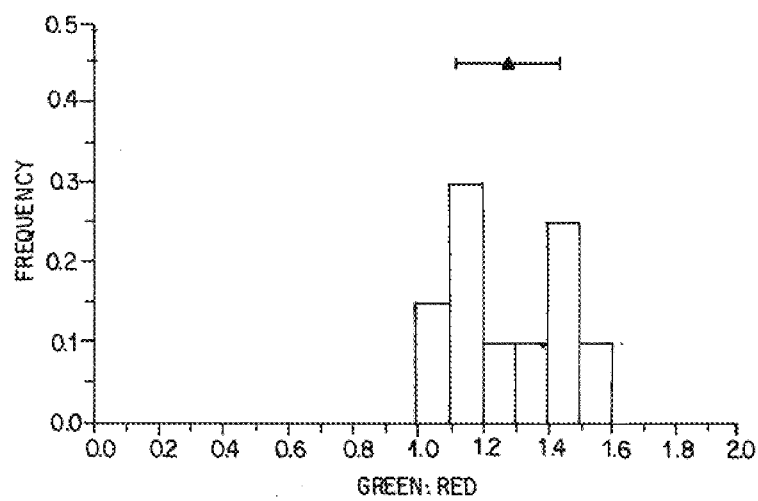
Figure 9E:
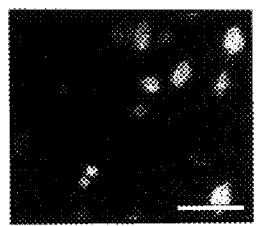
Figure 9F:
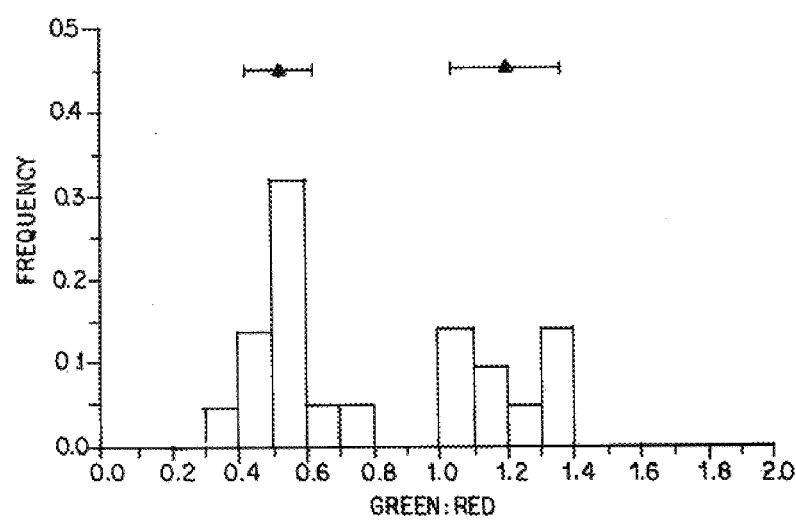

FIG. 8 (A) shows measurements of ultrasound backscatter amplitude for rat brain treated with photodynamic therapy. Tissue was examined ex vivo 1.5, 3, and 24 hours following photodynamic therapy. Results indicate increasing ultrasound backscatter with time compatible with the accumulation of post-therapy apoptotic cells. Bars labelled "−" correspond to non-irradiated controls whereas bars labelled "+" correspond to treated samples. Error bars indicate 1 standard deviation. FIG. 8(B) illustrates a representative ultrasound image of photodynamic therapy treated brain tissue examined ex vivo. The left panel corresponds to non-irradiated control tissue contralateral to the treated tissue shown in the right panel. The cone-shaped yellow area of increased ultrasound backscatter corresponds to the treated region. The tissue shown is freshly excised 24 hours after therapy and is not fixed. The contrast is equivalent to that obtained with samples fixed for histology. The panel width is 4 mm and the colour map indicated by the bar below the right panel is the same as for FIG. 4.

FIG. 9 illustrates representative results of fluorescence microscopy assaying for apoptosis. Images in the left column show composite images of propidium iodide and fluorescein fluorescence whereas right column panels present histograms of the ratio of integrated green staining to integrated red staining for cells cropped from fluorescence images. Images are background normalized. Top panels correspond to data for untreated rat brain—a negative control. Centre panels correspond to a DNase I digested rat brain slice serving as a positive control for end-stage apoptosis. The bottom panels correspond to the PDT-treated brain in the zone of high ultrasound backscatter. Approximately 40% of the cells exhibit green to red staining ratios consistent with the criterion for apoptosis determined from the positive control sample. The cells in this panel are interpreted as being in an early stage of apoptosis. The level of green staining in the cells increases two-fold after photodynamic therapy. Scale bar indicates 40 μm.

Figure 10:
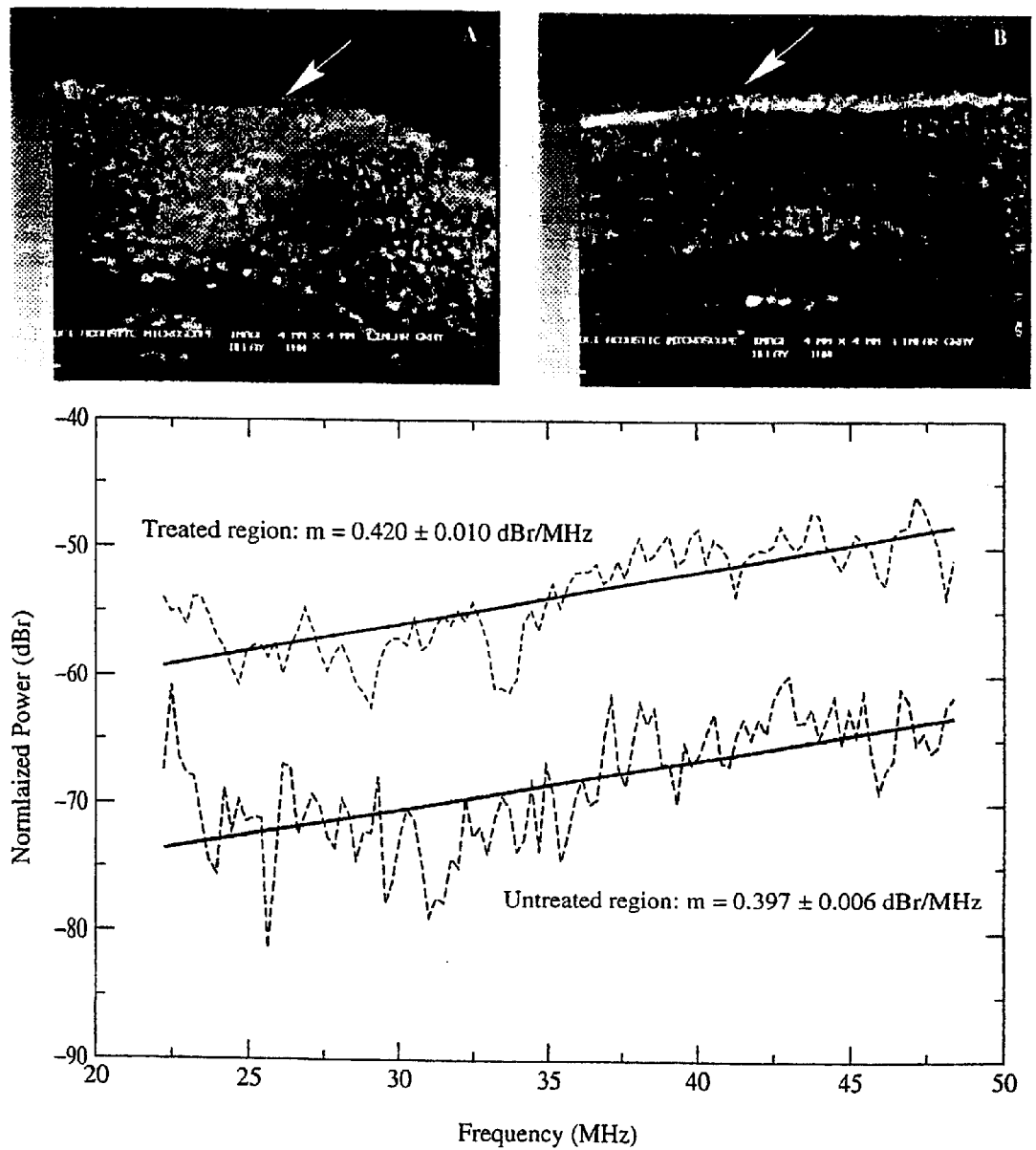
Figure 11A:
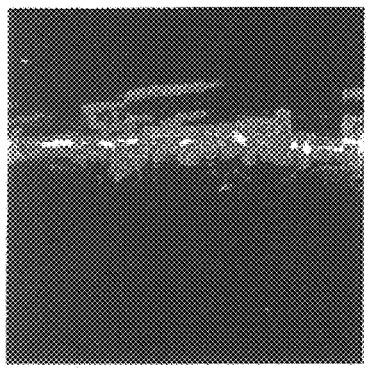
Figure 11B:
Figure 11C:
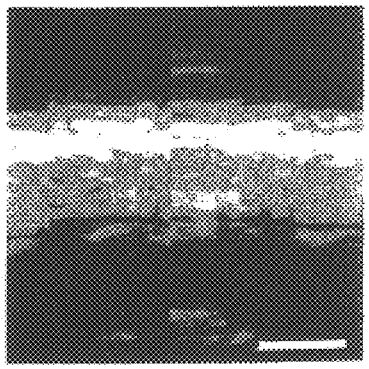
Figure 11D:
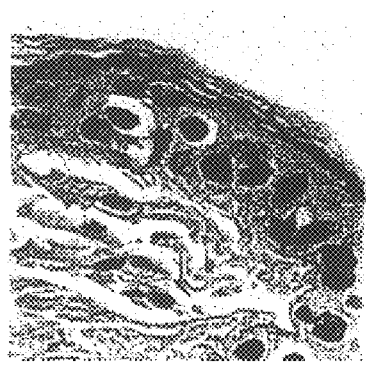
Figure 11E:
Figure 11D:

FIG. 10 illustrates treated (a) and untreated (b) regions of fresh ex-vivo rat brain taken 24 hours after photodynamic therapy treatment. Marks at the edge of each image are 0.5 mm apart. The treated region is observed as an area of increased brightness indicated by the white arrow in a). Normalized power spectra from regions of interest within treated and untreated areas are shown in the bottom panel. The mean and standard errors of the slope and intercept are given for each plot.

FIG. 11 illustrates imaging of apoptosis in vivo in rat skin exposed to varying doses of photodynamic therapy. Top panels present the results of ultrasound imaging whereas the bottom panels illustrate corresponding representative histological results. From left to right panels correspond to rat skin imaged in vivo 24 hours after exposure to 0, 8.5, and 17 J/cm$^2$ of activating laser light. The width of the top panels is 2 mm and the colour map shown below the right panel is the same used in all other figures. The most prominent increase in the top panels occurs at the epidermal surface with increasing dose. The epidermal layer is easily visualised in the left panel—it is the bright line at the top of the skin. An increase in the lower dermal region also occurs. Corresponding histology (FIG. 12b) shows prominent apoptotic cells with condensed and fragmented nuclei in the epidermal region in both the 8.5 and 17 J/cm$^2$ samples. A disruption of the cellularity in the dermal region below also occurs with dose. The scale bar indicates 20 μm.

Figure 12:
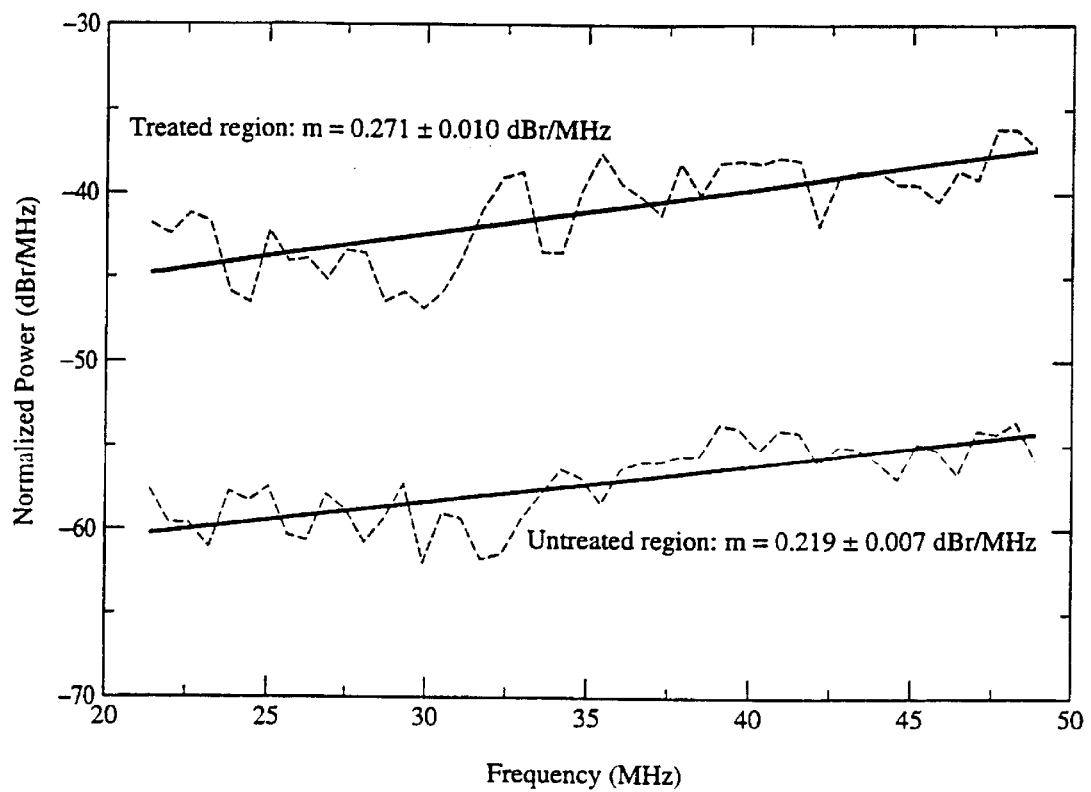

FIG. 12 shows the results of the frequency analysis from the rat skin experiment. The spectra were calculated in the same way as for FIGS. 6 and 10 except the window length was 1.5 mm and 20 independent radiofrequency A-scan lines were digitized. The slope of the average fitted normalized Fourier power spectrum was 23.7% greater for the treated skin (corresponding to the 17 J/cm$^2$ exposure in FIG. 11) than for the skin that was not exposed to light).

Figure 13:
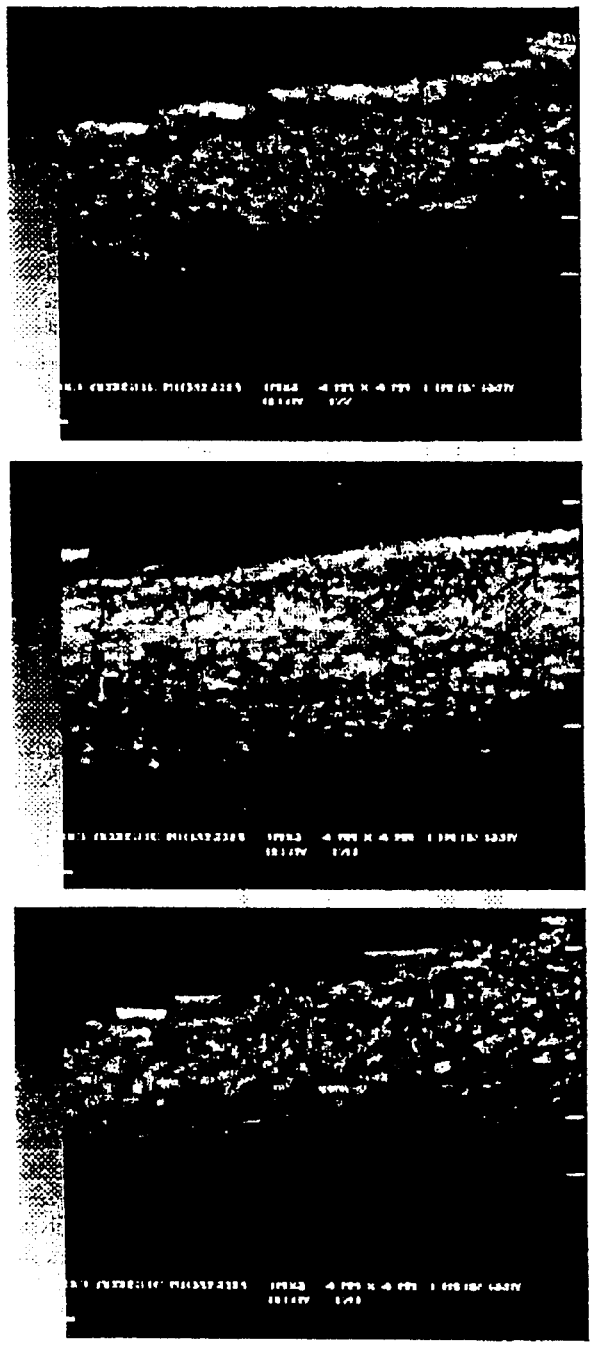

FIG. 13 illustrates a lymphoma with superficial extension into the skin. In the figure the top panel shows a lymphoma with superficial extension into the skin before treatment with a cocktail of four different anti-cancer drugs. The middle panel in the figure shows the tumour region imaged immediately after 24 hours infusion of chemotherapy intravenously. The bottom panel is an image of a non-tumour region near the tumour after administration of chemotherapy. The image brightness in the treated tumour area (middle panel) is greater than the brightness in either the untreated tumour (top panel) or the treated normal skin (bottom panel).

Embodiments of the invention are described by reference to the following specific examples which are not to be construed as limiting.

EXAMPLE 1

Comparison of Ultrasound Images for Normal, Apoptotic and Heat Killed Cells in-vitro This example demonstrates that ultrasound imaging can distinguish between cells undergoing apoptosis and those killed due to heating Apoptotic, viable and dead cells were prepared for ultrasonic imaging using a cell culture system. For each ultrasound imaging experiment four batches of approximately 10 human acute myeloid leukemia cells (AML-3) were grown at 37E C in α-minimal-media from frozen stock samples using 2 l roller flasks and 1.5 l of media. Culture growth was always initiated using frozen stock cells. In order to induce apoptosis two batches of cells were treated with cisplatin at a concentration of 10 μg/ml for 20 hours, a DNA intercalater, which causes p53-dependent apoptosis in this cell line. After 20 hours light microscopy, gel electrophoresis showing DNA-laddering and trypan blue staining were used to confirm that approximately 95% of the cells underwent apoptosis. Cells were washed in phosphate buffered saline (PBS), counted to ensure equal numbers of cells and pelleted in flat bottomed cryotubes at 800 g on a desktop swinging bucket centrifuge, producing pellets of the same size (diameter 1 cm, height 1 cm). Equal numbers of untreated cells were also pelleted in identical fashion. In order to produce dead cells, pelleted living cells were heat killed by incubating samples in a water bath at 65E for 15 minutes to ensure total cell kill. A pellet of apoptotic cells, already killed by programmed cell death was similarly heat-treated. The results of ultrasonic imaging were indistinguishable whether such pellets of cells were heat-treated or suspended cells were heat-treated and then pelleted. Heated samples were cooled in a water bath to room temperature prior to ultrasonic imaging.

Ultrasonic Imaging

Viable cells, heat-killed cells, apoptotic and heat-treated apoptotic samples of cells were imaged at room temperature using a commercially available Carl Zeiss Humphrey™ Research Diagnostic Ultrasound Biomicroscope (Carl Zeiss Canada) operating at a center frequency of 50 MHz. The probe was positioned such that the focal zone was at the same depth in each sample imaged and instrument settings were the same for each sample. Images were digitally recorded and a physical hardcopy was simultaneously produced. Pixel intensities were transformed to relative ultrasound backscatter amplitudes by multiplying by the inverse of the transfer function of the electronics of the biomicroscope, which was provided by the manufacturer. This method was necessary because the radiofrequency signals were not easily available for analysis on this commercial instrument. Image analysis was carried out using the Spider™ image processing package (Health Research Inc.)

Light Microscopy and Analysis

To confirm and investigate the morphology of cells, ultrasonically imaged and duplicate non-imaged samples were saved for haematoxylin and eosin staining by fixing in 10% (w/v) formalin in PBS and immediately processed as histological smears. No difference due to ultrasound imaging was observed. Samples of viable and apoptotic cells were additionally frozen in liquid nitrogen immediately after imaging and subsequently cryosectioned and stained with haematoxylin and eosin in order to confirm that the packing of cells in the two pellets was not significantly different. Light microscopy was carried out using a Leitz™ (Leitz Wetzlar Germany) 668 optical microscope coupled to a Sony CCD™ camera and recorded digitally on a Dell NetPlex™ 433/P (Dell Computer Inc.) using the Northern Exposure™ Image Analysis Software v2.9e (EMPIX Imaging Inc.). Cell packing was investigated from light microscopic images of cryosections by counting the number of cells in an area of the cryosections and indicated that packing was equivalent between the apoptotic and viable samples. To confirm the results obtained from cryosections, appropriate numbers of cells were pelleted in optically clear quartz cuvettes with a path-length of 0.200 cm. Cells at the inner glass surface were imaged using confocal microscopy and counted in accord with standard stereological procedures to ensure accurate and representative counts are obtained. To investigate the effect of packing, samples of apoptotic and viable cells were pelleted at 200 g, 800 g, and 3200 g and imaged with ultrasound in order to demonstrate that the results were consistent and independent of packing. Tests of statistical significance were carried out using the t-test. All experiments were carried out in duplicate and repeated. Image analysis of cryosections and cell counting was carried out using the Spider™ image processing package (Health Research Inc.).

Results and Discussion

Figure 1D:
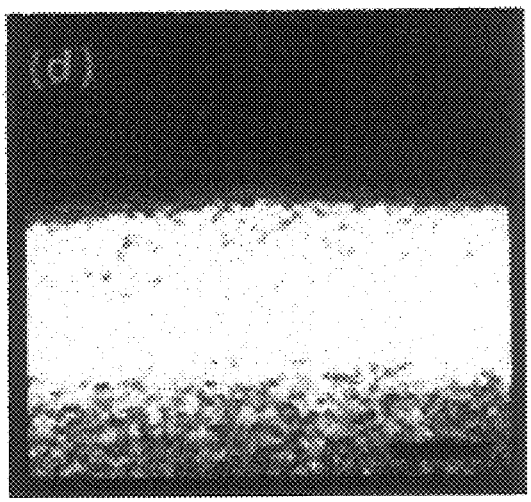
Figure 2A:
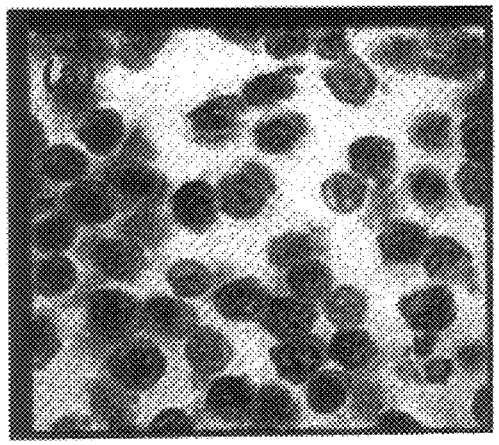
Figure 2B:
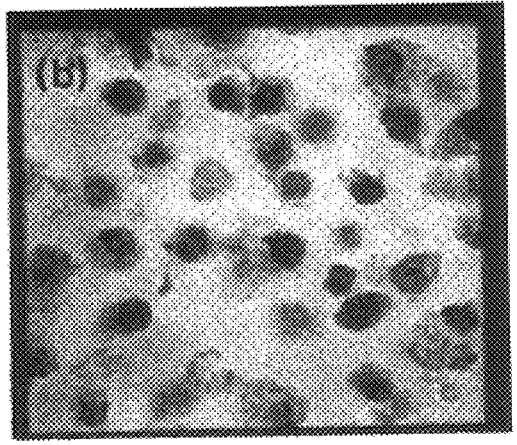
Figure 2C:
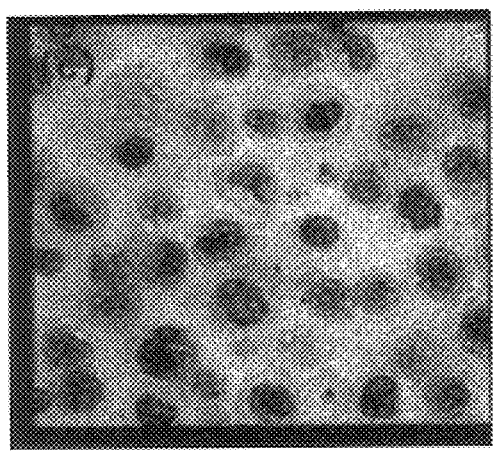
Figure 2D:
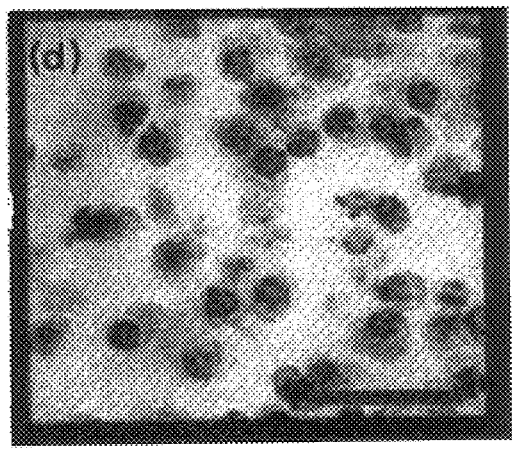

Four different samples of cells were imaged by ultrasound: apoptotic cells, viable cells, heat-killed cells, and an apoptotic sample of cells which had been treated by the same physical means, hyperthermia, used to produce the heat-killed cells. The ultrasonic images revealed visible differences between the apoptotic and viable cell samples (FIG. 1). Specifically, the apoptotic cells exhibited a brighter ultrasound speckle pattern in comparison to the viable cells, which, out of all samples, exhibited the least intense image (FIG. 1a). The ultrasonogram of the heat-killed cells exhibited an intermediate intensity, which was less than that of the apoptotic cells, which had been heat, treated (FIG. 1d). Of these four types of cells, the apoptotic sample consistently produced the brightest images with some regions saturated due to the normal operating range of the commercially available ultrasound biomicroscope used in this experiment.

The images obtained from the commercial ultrasonic imaging system are logarithmically compressed to achieve good contrast. Therefore to make relative backscatter measurements the pixel intensity values were 'decompressed' by the same logarithmic function. The results demonstrate an approximate two-fold difference in ultrasound backscatter signal between the viable and apoptotic cell samples (see Table 1 below). Moreover, this difference in scattering is underestimated due to saturation in the image of the apoptotic cells. The differences in mean backscatter amplitude between all samples were statistically significant (p=0.01). The samples were each moved 5 mm axially in the sound field with essentially no changes in relative backscatter intensities indicating attenuation effects to be minor.

Table 1 contains mean relative ultrasound backscatter amplitude in ultrasonic images of apoptotic, viable and heat-treated samples. Values were determined directly from images after compensating for a logarithmic compression used in the display process. All measurements were made using 5 images each and regions of 480×20 pixels in the focal band of each image. The differences between samples are statistically significant as described in the main text. The apoptotic sample was composed of 95% apoptotic cells. The heat-killed cells were essentially

TABLE 1

| Treatment | Mean Relative Ultrasound Backscatter Amplitude ± Standard Deviation | |
|---|---|---|
| | Viable Sample | Apoptotic Sample |
| Not heated | 55.8 ± 5.2 | 118.5 ± 1.5 |
| Heated | 81.1 ± 9.8 | 103.3 ± 1.5 |

The differences observed in the ultrasonic images appeared to be related to the striking sub-cellular morphological differences between the different cell samples (FIG. 2). Two samples, apoptotic and viable, were selected for further confirmatory analyses. Light microscopic images of apoptotic and viable cell sample cryosections indicated no gross differences in cell packing. Cell counting using standard stereological methods also indicated equivalent cell densities in the cryosectioned images of the apoptotic sample and the viable sample (76±5 and 74±3 cells in 8100 $\mu m^2$ section areas, respectively). This observation of equivalent cell packing in the apoptotic and viable samples was corroborated by cell counting from confocal microscopic images of cell samples in cross-section (not shown). Additionally, to investigate the consistency of the ultrasonic imaging, the preparation of the two different samples composed of viable and apoptotic cells was modulated. Samples were centrifuged at 200 g, 800 g, and 3200 g, yielding flocculent to compact pellets, and were then investigated by ultrasonic imaging. In each case there was a significant difference between the ultrasonograms of the apoptotic and normal samples, virtually identical to the initial results from pellets produced at 800 g. At 200 g, 800 g, and 3200 g the apoptotic samples produced backscatter amplitudes which were 2.11±0.3, 2.28±0.4 and 2.42±0.4 times greater than the viable samples, respectively. These values were similar to the 2.12±0.2 value determined for the original 800 g samples. This indicated that the imaging results were consistent and independent of cell packing.

The different image intensities observed here in association with the samples of differently treated cells could arise from two fundamental physical processes: differences in ultrasound scattering or differences in ultrasound attenuation. We suspect the former of the two processes since the intensity differences between the images are evident even at the top of the samples, where little attenuation would be expected. Differences in scattering could result from different distributions of scatters as proposed by computer-assisted numerical modeling. It has been suggested before that the cell's nucleus contributes significantly to ultrasound backscattering particularly if the nuclear material is condensed as in the pyknotic nuclei observed in the apoptotic cells. We suggest that the highly condensed clusters of nuclear material in the apoptotic cells contribute to the greater ultrasound scattering in the ultrasonograms of the apoptotic samples. In the viable cells the nucleus is intact and the nuclear material organized into a single spherical body with a diameter of approximately 5 $\mu$m (FIG. 2). Here the nuclear material is relatively optically diffuse and the nucleus is large nearly filling the entire cell. In contrast, in the apoptotic cells the nuclear material is condensed into many visible pyknotic bodies with sizes ranging from 0.5 to 3 $\mu$m in diameter (described in FIG. 2 description). These small pyknotic bodies, composed of condensed fragmented DNA and nucleoprotein, were visibly arranged in a more random fashion about the nuclear region of the apoptotic cells in comparison to the viable cell sample in which a single large nucleus makes up nearly the entire volume of the cell. Numerical modeling of ultrasound backscatter from ensembles of cells has demonstrated that under specific conditions signal strength increases with a randomization of scatterers, consistent with results of this experiment in which one scattering structure is transformed into many compact scatterers. According to backscattering theory, taking into account the Mie effect, such morphological differences that essentially divide a large scattering agent into a number of sufficiently small scattering units of equal aggregate volume should not result in an overall increased scattering for the imaging wavelengths used. For example, a break-up of a 5 $\mu$m nuclear scattering structure into 8 granules of 2.5 $\mu$m diameter (to maintain the volume) would not result in an increase in backscatter intensity for the 30 $\mu$m ultrasonic wavelength used.

The observed change in scattering could be caused by an increase in density and changes in compressibility of the scattering structures. During the apoptotic process the DNA-protein rich nucleus is enzymatically fragmented (FIG. 3) undergoing a very large increase in compaction similar to that which occurs during mitosis. This hypothesis is also concordant with prior investigations by other groups, which have demonstrated increased scattering from the hypoxic interior of living spheroid model-tumour systems characterized by cells with pyknotic nuclei.

The heat-killed sample exhibited a lesser increase in ultrasonic image intensity possibly due to a similar mechanism. This was evident in the predominance of granular features, absent in the unheated viable sample, which were not as visibly dense as the nuclear material in the apoptotic sample (FIG. 2). The heat-treated apoptotic sample exhibited an ultrasound backscatter amplitude intermediate between the heat killed an apoptotic cells. It is possible that heating cells may have resulted in changes of overall acoustical properties due to protein coagulation, which were not additive to the effects of apoptosis.

This experiment thus demonstrates the ability of ultrasound imaging to discriminate both dead versus living ensembles of cells and two different types of cell death: heat-induced and apoptotic. The particular method of inducing apoptosis in this experiment, by using cisplatin is representative of apoptosis in general as a response to cellular DNA damage. Cisplatin forms a variety of DNA adducts, the most prevalent of which is the 1,2-intrastrand crosslink. It has been estimated that there are approximately 10,000 platinum lesions on the genome using a dose sufficient to activate programmed cell death. The human cell line used in this experiment undergoes a p53-dependent apoptosis in response to cisplatin-mediated DNA damage in which the cellular DNA is condensed, and then enzymatically fragmented and exhibits a characteristic DNA fragmentation pattern (FIG. 3).

EXAMPLE 2

Measurement of Apoptosis in Human Leukemia Cell Line Exposed to Chemotherapeutic Drug with Comparisons to Mitotically Arrested Cells In order to demonstrate and characterize the ability of ultrasound imaging to detect apoptosis, a cell-culture system was utilized to permit carefully controlled experiments. The leukaemia cell line used, AML-5, undergoes a well-characterized p53-dependent apoptotic response to chemotherapeutic agents such as cisplatinum, which was used in this experiment. A maximal apoptotic response is reached 24 hours after the addition of the drug. At various timepoints after the addition of cisplatinum, cells were centrifuged into pellets 1 cm in height and visualized using a high-frequency ultrasound device. The instrument was operated at a center frequency of 40 MHz, permitting higher resolution imaging in comparison to conventional ultrasound devices operating at lower frequencies. Results presented in FIGS. 4 and 5 indicate that apoptotic cells scatter high frequency ultrasound at a level approximately 6 times (amplitude) that observed with non-apoptotic cells. The degree of scattering also exhibits a linear relationship to the proportion of apoptotic cells at each timepoint. The ultrasound backscatter amplitude begins to increase as the cells' nuclei condense approximately 2 to 3-fold in diameter over that of nuclei in non-apoptotic cells. The backscatter signal amplitude continues to increase to 6-times that obtained for normal cells with subsequent apoptotic nuclear fragmentation. Representative histological results presented in FIG. 5 indicate that these cells undergo a classic apoptotic response. Gross changes in morphology are observable, with changes in the nuclear membrane, nuclear condensation and nuclear fragmentation. We have demonstrated previously that increases in ultrasound image backscatter with apoptosis are due to such differences in cell morphology, and not due to potential differences in cell packing.

Mechanism of Ultrasound Detection of Apoptosis

Due to the observed correspondence of apoptotic nuclear condensation and of subsequent nuclear fragmentation with changes in ultrasound images we hypothesized that the nuclear material in the cells was responsible for the increased ultrasound backscatter. This hypothesis was further investigated using the same cell culture system, but with the pharmaco-active agent colchicine that produced condensed nuclear material in the form of metaphase chromosomes, but not fragmentation. In this series of experiments the drug arrested cells at the G2/M cell-cycle checkpoint in early mitosis. Cells exposed to colchicine for various timepoints were prepared, imaged and analyzed in the same way as for the apoptotic cells. Results are presented in FIG. 5. Whereas the ultrasound images of the apoptotic cells indicated a 6-fold increase in backscatter in comparison to normal cells, the mitotic cells exhibited an approximate 3-fold increase in ultrasound backscatter amplitude. By 24 hours a maximal cell-cycle arrest was visualized histologically and indicated by cytometric analysis to be approximately 30%—the maximal mitotic fraction that the cell line exhibited in response to colchicine.

This indicated that DNA condensation was associated with an increased ultrasound backscatter signal. In order to test whether the presence of condensed DNA was necessary a different series of experiments was devised; the results of which are presented in FIG. 5(B). These experimental conditions tested the hypothesis that if indeed DNA condensation was responsible for the noted increase in ultrasound backscatter then enzymatically removing the DNA condensation should reduce the ultrasound signal to normal. Thus colchicine treated cells which had been exposed to the drug for 24 hours, the first timepoint at which mitotic arrest was maximal, were treated with an excess of DNase I in the presence of a mild permeabilizing agent. Appropriate controls and histological analyses were included to ensure the drop in ultrasound backscatter signal towards that of the normal cells were a result of the DNase activity and not the activity of the permeabilizing agent. Using two different concentrations of DNase the ultrasound backscatter was found to drop towards a level similar to that of the untreated cells consistent with the interpretation that DNA-nuclear condensation was responsible for the increase in backscatter.

Since it was not possible enzymatically nor mechanically to fragment the condensed nuclei above into an apoptotic pattern in which 5–10 fragments are produced and marginated at the periphery of the apoptotic cell, we used numerical modelling to attempt to explain the changes in ultrasound backscatter between the apoptotic cells and the untreated cells. We postulated that the initial increase in ultrasound backscatter after treatment with cisplatinum for 6 hours was due an early stage of apoptosis where the cells exhibit primarily nuclear condensation, and that the further two-fold increase in ultrasound backscatter exhibited by the apoptotic cells at 24 hours was a result of their nuclear fragmentation. Using an established numerical modelling system an array of cells was simulated. Apoptosis was modelled in two steps. The nucleus was first condensed in diameter and then fragmented into 4–8 scatterers in the second step. For each array of cells the ultrasound backscatter was computed. The results obtained indicate that the scattering of ultrasound from the array with condensed nuclei was between 2 to 3 times that of the normal cell array whereas breaking the condensed nucleus into 4–8 scatterers increased the ultrasound backscatter to 6 times the value for normal cells, in good agreement with the experimental results.

The results of the frequency analysis of the radiofrequency data from the normal and apoptotic cells is shown in FIG. 6 calculated according to the method described above. The apoptotic cells exhibit a 67.8% increase in the slope of the average fitted normalized Fourier spectrum as compared to normal cells. This frequency analysis was extended to calculate the effective scatterer size using the method of Lizzi et al (Supra). The effective scatterer size was clacu- lated to decrease by 47% due to apoptosis which is consistent with our histological findings that the nuclear material is condensed into smaller pieces of material in apoptotic cells.

Discussion

This experiment demonstrates that apoptosis is detectable using high frequency ultrasound imaging. In this investigation we have been able to demonstrate the ultrasonic detection of apoptosis in vitro.

The in vitro experiments implicate the cell's nuclear chromosomal material as the major source of ultrasound scattering. This is not necessarily surprising since in the chromosome the fundamental repeating subunit of chromatin, the nucleosome, is comprised of a protein density of 1.3 g/cm$^3$, and a DNA density of 1.7 g/cm$^3$ in approximately equal proportions. Some 25 million of the protein units in combination with 2 m of DNA are packed into chromosomes, which are approximately 6–8 μm in length when condensed. The process of nuclear condensation, which takes place in the early stages of apoptosis, similar to mitosis, compacts chromosomes from forms which are distributed throughout most of the cell's nucleus to more canonical condensed forms. Other previous studies also support the postulate that the cellular nuclear material is the major scatterer of high frequency ultrasound. Direct evidence providing strong evidence for this hypothesis to be correct is presented in this experiment where the induction of DNA condensation and enzymatic degradation of condensed DNA demonstrates such condensation to be sufficient and necessary to obtain an increased ultrasound backscatter. However, in our experiments the mitotically enriched population of cells never exhibited as great an increase in ultrasound backscatter as did the apoptotic cells. This is consistent with the result that cells in early apoptosis, at 6 hours after cisplatinum treatment, also scatter ultrasound less than in later stages, which have fragmented nuclei. Specifically, the late-phase apoptotic cells with fragmented nuclei scattered ultrasound approximately twice as much as the early phase apoptotic cells, with only condensed nuclei. This was best accounted for by using a mathematical simulation of the effects of fragmenting a condensed nucleus. The most plausible reason for such increases could be linked to the randomization of scatterers, which would occur with apoptotic nuclear fragmentation. In our simulations the condensing of the nucleus increased the signal intensity by 2 to 3 times depending on whether the nucleus was simulated using 16 or 64 point-scatterers. By randomizing the position of such a pyknotic nucleus through out the cell into 4–8 granules of scatterers the ultrasound signal further increased to a level 6 times greater than for the normal cells. These values are very close to the 2.92 and 5.83-fold increases in ultrasound backscatter determined experimentally for the early-phase apoptotic cells at 6 hours exhibiting nuclear condensation, and the late-phase apoptotic cells exhibiting granules of nuclear fragmentation, respectively.

EXAMPLE 3

Measurement of Apoptosis in Rat Brain Exposed to Photodynamic Therapy

To determine whether ultrasound imaging could be used to detect apoptosis which had occurred in vivo we applied the technique to monitor apoptosis ex vivo in an animal system which involved photodynamic therapy. This type of therapy has been demonstrated to induce apoptosis in several tissues. In this experiment, photodynamic therapy using a hematoporphyrin derivative was applied in a rat model system. After treatment with photofrin to light-sensitize animals, a small hole was drilled in the cranium of the anaesthetized animal, and a section of the brain was irradiated with laser light to activate the photodynamic sensitizer. The animal's brain was extracted and imaged ultrasonically formalin fixed or unfixed. After an investigation of dose and time effects three separate timepoints were chosen to monitor the tissue response: anaesthetized animals were sacrificed 1.5 hours, 3 hours, and 24 hours after photodynamic therapy. Ultrasound backscatter measurements made at all timepoints, in conjunction with ultrasound images obtained at the 24 hour timepoint at the site of therapy and in the non-irradiated contralateral side of an unfixed freshly excised brain are shown in FIG. 8a. The corresponding images are shown in FIG. 8b where the left panel is untreated bain and the bright region in the right panel image is the treated region. Backscatter amplitude measurements indicate that the 1.5, 3 and 24 hour post-photodynamic therapy brain areas exhibited a 2.1±1.1, 3.3±1.6, and 3.7±2.0 fold increase in ultrasound backscatter in comparison to individualized controls. The 24 hour tissues were selected for histological analysis since ultrasound results were consistent with a maximal amount of apoptosis in this sample. Since scoring from haematoxylin and eosin stained sections of brain sections was determined to be too subjective in our hands a specific staining procedure was used to detect apoptosis. The procedure involved labelling the free DNA ends produced by apoptotic DNA fragmentation with a green fluorescent stain. A second marker, propidium iodide, which stains cytoplasm with red fluorescence was also used. Composite images of red and green fluorescence of representative areas that were treated and not treated are shown in FIG. 9. A positive control, generated by enzymatically fragmenting DNA to produce an excess of free ends similar to those generated during apoptosis is also shown. A simple assay was utilized where the calculated ratios of green to red staining intensity correlated with the presence or absence of apoptosis. Using a computer the level of green to red fluorescent staining was determined for the cells in the tissue sections. The treated brain section showed two statistically significant populations of cells which were clustered distinctly below and above the apoptotic threshold value of 1 in terms of their green to red staining ratios. Using this value, the analysis indicated approximately 40% of the cells to be apoptotic in the treated region. This level of ultrasound backscatter increase corresponded well to cell culture experiments, which indicated compatible increases in ultrasound backscatter with apoptosis.

Referring now to FIG. 10, wherein there are illustrated results obtained in ex-vivo rat brains exposed to PDT. FIG. 10a shows a region of untreated brain while b) shows the treated region that is evident by the region of high (bright) signal. The signal amplitude from this region is approximately 6 times higher than from the untreated area. Taking the bright region as our region of interest, we calculated the Fourier power spectrum of the radio frequency data from this region and normalized it by dividing this transform by the Fourier power transform of a reference pulse measured from a quartz flat using the same transducer. FIG. 10c shows the normalized frequency spectrum of both treated and untreated regions. The apoptosis is confirmed by the fact that the slope of the scatter signal versus frequency becomes more positive after treatment of the brain. Apoptosis was independently confirmed in the treated region using fluorescent cell staining techniques. No apoptosis was observed in the untreated region.

EXAMPLE 4
Measurement of Apoptosis in Rat Skin Exposed to Photodynamic Therapy Including Effect of Varying Light Dose To demonstrate the feasibility of detecting apoptosis in vivo additional experiments were carried out in which a photofrin light sensitized rat had areas of its skin exposed to activating laser light. Areas of skin exposed to 0, 17, and 8.5 J/cm$^2$ were imaged (FIG. 7) in sedated living animals and resulted in ultrasound backscatter levels that corresponded with the dose of activating light. At 0, 8.5 and 17 J/cm$^2$ measurements of ultrasound backscatter amplitude from the epidermis were 12.8±4.3, 59.8±17.0, and 32±6.4, respectively. This part of the skin, which scatters more prominently that the underlying dermis, can be readily identified since the resolution of the instrument axially is 38 $\mu$m. Histological analyses revealed increasing levels of apoptosis with the dose of activating light (FIG. 7). Consistent with ultrasound levels indicating a marked backscatter response at the epidermal surface the most prominent levels of apoptosis were exhibited in the superficial cellular layers of the epidermis. Apoptotic cells were easily visible with haematoxylin and eosin staining and confirmed using fluorescent staining for apoptosis. However, increased backscatter was also observed with increasing dose from a less superficial zone consistent with the papillary and reticular layers of the dermis. In this zone the cellular components, fibroblasts and leukocytes, appear to undergo cell death with photodynamic therapy resulting in a disruption of the dermal layer. This may account for the increased backscatter seen deep into the tissue away from the cellular epidermis, which becomes apoptotic with photodynamic therapy.

In rat skin experiments skin from the dorsal posterior of the animal was shaved. A 1 cm diameter area was exposed to 0, 8.5, or 17/cm$^2$ with an irradiance of 100 mW/cm$^2$. Animal were kept in a dark environment before and after treatment. Living animals were imaged in a sedated state 24 hours after treatment. Skin biopsies were obtained and submitted for histological analyses. Apoptosis was rat skin was easily visualized in haematoxylin and eosin stained sections. Fluorescently labelled sections were analyzed confirming the presence of apoptosis.

Discussion of Examples 3 and 4

Experiments described in examples 3 and 4 demonstrate that apoptosis is detectable using high frequency ultrasound imaging. In this investigation we have been able to demonstrate the ultrasonic detection of apoptosis in tissues ex vivo (in rat brain) and in-vivo (in rat skin).

In this work, photodynamic therapy treated brain tissue was examined ex vivo and the ultrasound imaging technique was used to image skin tissue in vivo in a living animal, treated to induce apoptosis. The role of photodynamic therapy in inducing apoptosis is currently under investigation. Nevertheless, the ultrasound results in this experiment coupled with apoptosis-specific fluorescent labelling and analysis of histological sections supports a role for apoptosis in the response to PDT of brain tissue and skin tissue in this experimental system, consistent with other investigations. In this experiment the use of ultrasound imaging to detect apoptosis in response to a treatment in tissue represents the first evidence of such a modality detecting programmed cell death ex vivo and in vivo induced in a living organism. Since most chemotherapeutics are now recognized to induce apoptosis in tumours, one may envisage the ultrasound imaging method being used to rapidly evaluate the effects of treatment regimens in vivo. The ultrasound imaging approach, as demonstrated in this experiment, could provide the clinician with direct and quantitative non-invasive measures of cellular response directly after chemotherapy is administered rather than waiting for a complete course of treatment to be finished before clinically assessing outcome.

In conclusion, in this experiment high-frequency ultrasound imaging was used to detect apoptosis induced by anti-cancer agents in vitro, and to visualize programmed cell death ex vivo and in vivo. Experimental evidence corroborated by numerical modelling supports the basis for the ultrasonic detection of programmed cell death to be the subcellular nuclear changes that cells undergo during apoptosis. The results indicate that such subcellular structural changes can have profound influences on ultrasound images and demonstrate the possibility of rapidly and non-invasively monitoring the effects of chemotherapeutic agents and other anti-cancer treatments using an ultrasound based approach.

Methods for Examples 2,3 and 4

Cell Preparation

All cells were prepared for ultrasound imaging using a cell culture system. For any experimental timepoint or condition experiments were completed in quadruplicate. For each experiment, approximately $1 \times 10^9$ human acute myeloid leukaemia cells (AML-5) were grown at 37° C. in 300 ml-minimal-media always from frozen stock samples.

To induce apoptosis 5 batches of cells were exposed to the cisplatinum at 10 $\mu$g/ml. This drug is a DNA intercalater that causes a p53-dependent apoptosis in this cell line. Cells were treated with cisplatinum for 0, 6, 12, 24, and 48 hours. To confirm apoptosis was taking place the 24 hour sample was examined using light-microsopy, gel-electrophoresis showing DNA laddering, and trypan-blue staining, confirming that approximately 95% of the cells underwent apoptosis at this timepoint. Cells were washed in phosphate-buffered saline and counted to ensure equal numbers of cells. Preparations were subsequently pelleted in flat bottom cryo-tubes at 800 g on a desktop swinging bucket centrifuge. All pellets were the same size, with a diameter of 1 cm and a height of 1 cm.

To arrest cells in mitosis, effectively enriching the mitotic fraction in the cell population, cells were treated with colchicine at a concentration of 0.1 $\mu$g/ml. By inhibiting microtubule formation this drug arrests dividing cells at the G2/M checkpoint of the cell cycle, corresponding to metaphase of mitosis. In this cell culture system the maximal enrichment of the mitotic population is an increase to approximately 30%.

For investigations of DNA condensation effects on ultrasound backscatter pellets of mitotically enriched cells were taken and resuspended in 1 ml of PBS. As controls, samples were treated with only DNase I™ (Pharmacia) alone at concentrations of 5,413 U/ml and 10,826 U/ml. and only Triton™ X-100 (Sigma) at a concentration of 0.1% (w/v). In order to permeabilize cells and permit DNase I™ to enter the cells, samples were treated with both DNase I™ and Triton™ x-100 at the concentrations given above. Digestions proceeded for 30 minutes and were terminated by adding EDTA to a final concentration of 500 mM. All samples were assessed histologically.

To help characterize the effects of the drugs, cytometry was carried out using nuclei from approximately $3 \times 10^5$ cells. Cells were lysed after resuspension in 1 ml isotonic buffer (0.2% Triton X-100 in PBS-citrate, 0.1 mg/ml RNase A, 0.05 mg/ml propidium iodide) to release the nuclei. This suspension was strained through a fine gauze mesh to remove cell debris. Following a 30 minute incubation at 4° C. in the dark, the samples were analyzed on a Becton-Dickenson flow cytometer. A cell cycle analysis program, CellFIT™ 2.01.2 (SOBR), was used to quantify cells with respect to the different phases of the cell cycle.

Light Microscopy and Analysis

To confirm and investigate the morphology of cells at each experimental condition, ultrasonically imaged and duplicate non-imaged samples were saved for hematoxylin and eosin staining by fixing 12 hours in 10% (w/v) formalin in buffered saline. These cells were embedded in paraffin and processed as histological sections. No histological differences due to ultrasound imaging were observed. Images of pellet cryosections were obtained to confirm that no differences in packing were present.

Light and fluorescence microscopy was carried out using a Zeiss Axioscope™ 20 (Carl Zeiss, Germany). This microscope was coupled to a colour SONY CCD™ camera and recorded digitally on an IBM™ PC using the Northern Eclipse™ Image Analysis Software 1.1 (EMPIX Imaging Inc.).

Ultrasound Imaging

All cell samples and animal tissue samples were imaged at room temperature immersed in buffered isotonic saline using a custom built high-frequency ultrasound instrument operating at 40 MHz. Living animals were images using high viscosity ultrasound gel (ATL Inc., Reedsville Pa.) over areas of skin. The focal depth of the instrument is 9 mm, it's axial resolution is 37 $\mu$m and it's lateral resolution, limited by the ultrasound beam width, is 55 $\mu$m. The ultrasound probe was positioned such that the focal zone was the same depth in each imaged specimen. All images were digitally recorded and a physical hard copy was simultaneously produced.

Quantitative Analysis of Ultrasound Backscatter

The quantitative degree of ultrasound backscatter for each timepoint was assessed in two manners. In this first, pixel intensities were transformed to relative ultrasound backscatter amplitudes by multiplying the inverse of the transfer function of the electronics of the ultrasound imaging instruments. This corresponds directly to the degree of ultrasound backscatter amplitude. In the second method A-scans, the individual line scans that are processed to produce two-dimensional ultrasound images were obtained and assessed. Such A-scans are also independent of the instrument's image processing and amplification processes. Since both methods provided equivalent results the former was used since it did not require the lengthy collection of radio-frequency data and could be more readily used with living animal specimens.

Mathematical Simulations

Two-dimensional mathematical simulations were carried out using an established system which simulates a pseudo-random array of point scatterers similar to packed cells with an average cellular diameter of 7 $\mu$m. The nucleus was modelled by 16 or 64 regular point scatterers with equal separations randomized in position by 20% of the cellular diameter. A full investigation of scatterer sizes and effects of randomization was carried out but for the purposes of this investigation based on histological observations apoptosis was simulated in two phases. In the first, the cells nucleus was condensed from 75% of the cell's diameter to 40% of the diameter and randomized in position within the cell. In the second phase this nucleus was fragmented into 4, 6 and 8 fragments which were also randomized within the cell. The interaction of ultrasound with the array of simulated scatters was carried out using ultrasound parameters matching experimental conditions used. A more detailed explanation of the methodology is presented elsewhere.

Photodynamic Therapy and Fluorescence Analysis

Male Fisher rats were treated with 12.5 mg/kg of photofrin injected intraperitoneally and were kept in a dark environment for 24 hours prior to irradiation. One 4 mm holes was then created in each side of the rat's cranium avoiding mechanical stress to the underlying cortex. This area was then treated using for 30 seconds using a red laser light with a wavelength of 632 nm and a spot size of 2 mm in diameter. This spot size was selected in order to be. readily visualized in the 4 mm scan width of the ultrasound microscope next to an untreated region. Several treatment irradiances were experimented with including 1, 3, 5, and 17 J/cm². To minimize post-therapy cerebral swelling and still show a sufficient response to therapy 3 J/cm² was selected for further experiment. The optical power irradiance at the dural surface was 100 mW/cm². Methods used in animal surgery are the same as published elsewhere.

The animals were sacrificed at 3 timepoints: 1.5, 3, and 24 hours after the above photodynamic therapy. The first two timepoints surveyed early treatment effects. The last time was chosen since earlier experimentation seemed to suggest an accumulation of cells arrested in relatively early stages of apoptosis after 8 hours post photodynamic therapy treatment. Equivalent results were obtained whether the rat brains were formalin fixed prior to ultrasound imaging in order to minimize degradation effects, or imaged ultrasonically prior to fixation.

For general pathological analysis rat brains were sectioned and hematoxylin and eosin stained. To specifically assess for the effects of apoptosis an enzymatic method was used which with terminal-deoxynucleotidyl-transferase in order to label the 3'-OH ends of fragmented DNA with fluorescein-12-dUTP. Since ultrasound analyses of the post-therapy 24-hour specimen were most consistent with the highest levels of putative apoptosis, this specimen was subjected to the apoptosis labelling assay. As a positive control a PDT-untreated rat brain section was treated with proteinase-K and DNase I at a concentration of 1 µg/ml and incubated at room temperature for 10 minutes prior to having sections stained using the enzymatic approach. This method results in about 80% positive green-staining cells in the control section but may stain control cells more intensely that apoptotic cells. As a negative control contralateral sections of the PDT-treated rat were used. Sections of the PDT-exposed rat brain were also stained in this fashion. All sections were counterstained with propidium iodide which stains both apoptotic and non-apoptotic cells red throughout the cytoplasm. Slides of sections were visualized immediately after staining. Microscopy was carried out as above using a standard fluorescein filter set (520±20 nm) whereas an appropriate filter (>620 nm) to detect fluorescein and propidium iodide staining, respectively. Images of red and green fluorescence were captured separated and added together to form composites. In order to analyze the fluorescence levels within cells in the sections a computerized approach was used to crop cells after automatic contouring and to quantitatively determine separate levels of red staining and green staining within each cell. These integrated values were then corrected by normalization for slightly different red and green fluorescent background staining values. Image analysis was carried out on IBM PC running Aldus Photostyler Version 2.0.

EXAMPLE 5

Detection of Apoptosis in Tumour Nodules in Patient with Lymphoma Undergoing Chemotherapy The desired action of chemotherapeutic drugs is to kill tumour cells. Almost all chemotherapeutic agents are now recognized to kill target neoplasms by inducing apoptosis—programmed cell death. We have conducted imaging experiments in human cancer patients in order to demonstrate that apoptotic responses of tissues to chemotherapy can be detected using high-frequency ultrasound imaging. In the figure on the following page the top panel shows a lymphoma with superficial extension into the skin before treatment with a cocktail of four different anti-cancer drugs. One of these drugs is cisplatinum—which induces apoptosis by causing damage to the DNA of tumour cells. Cisplatinum's effect on cells and the corresponding changes in ultrasound images have been characterized by us previously. The middle panel in the figure shows the tumour region imaged immediately after 24 hours infusion of chemotherapy intravenously. The increased brightness in the image is compatible with an apoptotic response in the tissue. The bottom panel is an image of a non-tumour region near the tumour after administration of chemotherapy and indicates that the apoptosis that occurs is tumour specific (tumours of the lymph glands) at various stages of their cancer treatment. Preliminary results indicate that ultrasound imaging can detect the apoptotic cell death induced by chemotherapy. In the figure on the following page the top panel shows a lymphoma with superficial extension into the skin before treatment with a cocktail of four different anti-cancer drugs. One of these drugs is cisplatinum—which induces apoptosis by causing damage to the DNA of tumour cells. Cisplatinum's effect on cells and the corresponding changes in ultrasound images have been characterized by us previously. The middle panel in the figure shows the tumour region imaged immediately after 24 hours infusion of chemotherapy intravenously. The increased brightness in the image is compatible with an apoptotic response in the tissue. The bottom panel is an image of a non-tumour region near the tumour after administration of chemotherapy and indicates that the apoptosis which occurs is tumour specific. Computerized tomographic imaging has been used clinically to indicate that the tumour has responded to therapy, as demonstrated by the ultrasound images, and has shrunk in size as a result of chemotherapy.

The invention may be varied in any number of ways as would be apparent to a person skilled in the art and all obvious equivalents and the like are meant to fall within the scope of this description and claims. The description is meant to serve as a guide to interpret the claims and not to limit them unnecessarily.

What is claimed is:

1. A non-invasive method of monitoring apoptosis in cell culture or tissues using ultrasound imaging, comprising the steps of:

1.) imaging a selected site of the culture or tissues using high frequency ultrasound imaging to obtain a first image;

2.) exposing the selected site to an apoptosis-inducing stress;

3.) imaging the selected site, or a portion thereof, using high frequency ultrasound imaging at subsequent timed intervals to obtain a second image;

4.) measuring a signal amplitude of a region of interest of the selected site in said first and said second images;

5.) comparing the signal amplitude measurements for the regions of interest in said first and said second images and determining whether said second image region exhibits an increase in amplitude which is an indication that apoptosis has begun; and 6.) measuring a change in a frequency spectrum of an ultrasound backscatter signal in the region of interest between said first and said second images and confirming that apoptosis has begun when a slope of an average of the normalized frequency spectrum has increased, wherein said high frequency ultrasound imaging is at a frequency greater than 20 MHz.

2. A method as defined in claim 1 comprising the additional step of calculating an average scatterer size from the frequency spectra collected and further confirming apoptosis when there is a decrease in the average scatterer size in the region of interest.

3. A method as defined in claim 2, wherein a decrease of between 20–50% in average scatterer size is indicative of apoptosis.

4. A method as defined in claim 3, wherein a decrease of at least 30% in average scatterer size is indicative of apoptosis in cells while a decrease of at least 20% is indicative of apoptosis in tissues.

5. A method as defined in claim 1, wherein an increase in amplitude by at least a factor of 3 is indicative of apoptosis in step (5).

6. A method as defined in claim 5, wherein the increase in amplitude is by a factor of between 3 and 6.

7. A method as defined in claim 1, wherein an increase in said slope of at least 80% for cells and 5% for tissues is indicative of apoptosis.

* * * * *